(12) United States Patent
Jang et al.

(10) Patent No.: US 9,790,240 B2
(45) Date of Patent: *Oct. 17, 2017

(54) LIGAND COMPOUND, A PREPARATION METHOD THEREOF, A TRANSITION METAL COMPOUND, AND A PREPARATION METHOD THEREOF

(71) Applicant: LG CHEM, LTD., Seoul (KR)

(72) Inventors: Jae Kwon Jang, Daejeon (KR); Hyo Jung Han, Daejeon (KR); Ki Won Han, Daejeon (KR); Seul Ki Kim, Daejeon (KR); Eun Jung Lee, Daejeon (KR); Choong Hoon Lee, Daejeon (KR); In Sung Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/649,486

(22) PCT Filed: Nov. 19, 2013

(86) PCT No.: PCT/KR2013/010512
§ 371 (c)(1),
(2) Date: Jun. 3, 2015

(87) PCT Pub. No.: WO2014/092352
PCT Pub. Date: Jun. 19, 2014

(65) Prior Publication Data
US 2016/0215004 A1    Jul. 28, 2016

(30) Foreign Application Priority Data

Dec. 11, 2012 (KR) .................. 10-2012-0143806
Dec. 11, 2012 (KR) .................. 10-2012-0143809
Nov. 18, 2013 (KR) .................. 10-2013-0140006

(51) Int. Cl.
C07F 7/08      (2006.01)
C07F 17/00     (2006.01)
C07F 7/00      (2006.01)
C08F 4/659     (2006.01)

(52) U.S. Cl.
CPC .............. *C07F 7/0812* (2013.01); *C07F 7/00* (2013.01); *C07F 7/006* (2013.01); *C07F 17/00* (2013.01); *C08F 4/65908* (2013.01); *C08F 4/65912* (2013.01)

(58) Field of Classification Search
CPC .................................................... C07F 7/0812
See application file for complete search history.

(56) References Cited

U.S. PATENT DOCUMENTS

| 5,064,802 A | 11/1991 | Stevens et al. |
|---|---|---|
| 5,905,162 A | 5/1999 | Lin |
| 7,834,205 B2 | 11/2010 | Resconi et al. |
| 7,858,717 B2 | 12/2010 | Resconi et al. |
| 2009/0171047 A1 | 7/2009 | Resconi et al. |
| 2009/0186995 A1 | 7/2009 | Canich et al. |
| 2009/0275712 A1 | 11/2009 | Resconi et al. |
| 2011/0152529 A1 | 6/2011 | Lee et al. |

FOREIGN PATENT DOCUMENTS

| EP | 0728773 A1 | 8/1996 |
|---|---|---|
| EP | 1462464 | 9/2004 |
| EP | 2103634 A1 | 9/2009 |
| JP | 2005-528412 A | 9/2005 |
| JP | 2009-530341 A | 8/2009 |
| JP | 2009-533382 A | 9/2009 |
| JP | 2014-505136 A | 2/2014 |
| KR | 1020000076111 | 12/2000 |
| KR | 1020010101034 | 11/2001 |
| KR | 1020050085300 | 8/2005 |
| KR | 100820542 | 4/2008 |
| KR | 1020080065868 | 7/2008 |
| KR | 100986301 | 10/2010 |
| KR | 100999592 | 12/2010 |
| KR | 1020110013286 | 2/2011 |
| WO | 2012084961 | 6/2012 |

OTHER PUBLICATIONS

Camille Descour et al., 'Catalyst behaviour for 1-pentene and 4-methyl-1-pentene polymerisation for C2-, Cs- and C1-symmetric zirconocenes', Polym. Chem., 2011, 2, 2261-2272.

Colin L. Beswick et al., Metal-Alkyl Group Effects on the Thermodynamic Stability and Stereochemical Mobility of B (C6F5)3-Derived Zr and Hf Metallocenium Ion-Pairs, J. Am. Chem. Soc. 2000, 122, 10358.

*Primary Examiner* — Noble Jarrell
*Assistant Examiner* — John S Kenyon
(74) *Attorney, Agent, or Firm* — Dentons US LLP

(57) ABSTRACT

The present invention relates to a novel ligand compound, a preparation method thereof, a transition metal compound including the ligand compound, and a preparation method thereof. The ligand compound of novel structure according to the present invention and the transition metal compound including the same may be used as a polymerization reaction catalyst for preparing olefin polymers.

4 Claims, No Drawings

LIGAND COMPOUND, A PREPARATION METHOD THEREOF, A TRANSITION METAL COMPOUND, AND A PREPARATION METHOD THEREOF

This application is a National Stage Application of International Application No. PCT/KR2013/010512, filed Nov. 19, 2013, and claims the benefit of Korean Application No. 10-2012-0143806, filed on Dec. 11, 2012, Korean Application No. 10-2012-0143809 filed on Dec. 11, 2012, and Korean Patent Application No. 10-2013-0140006, filed on Nov. 18, 2013, all of which are hereby incorporated by reference in their entirety for all purposes as if fully set forth herein. This application is a National Stage Application of International Application No. PCT/KR2013/010512, filed Nov. 19, 2013, and claims the benefit of Korean Application No. 10-2012-0143806, filed on Dec. 11, 2012, Korean Application No. 10-2012-0143809 filed on Dec. 11, 2012, and Korean Patent Application No. 10-2013-0140006, filed on Nov. 18, 2013, all of which are hereby incorporated by reference in their entirety for all purposes as if fully set forth herein

BACKGROUND OF THE INVENTION (a) Field of the Invention

The present invention relates to a novel ligand compound, a preparation method thereof, a transition metal compound including the ligand compound, and a preparation method thereof. This application claims the benefit of Korean Patent Application No. 10-2012-0143806, filed in the Korean Intellectual Property Office on Dec. 11, 2012, Korean Patent Application No. 10-2012-0143809, filed in the Korean Intellectual Property Office on Dec. 11, 2012, and Korean Patent Application No. 10-2013-0140006, filed in the Korean Intellectual Property Office on Nov. 18, 2013, which are all hereby incorporated by reference in their entireties into this application.

(b) Description of the Related Art

For a long time, there have been many advances in metallocene catalyst for olefin polymerization. Metallocene compounds are generally activated by an aluminoxane, a borane, a borate, or other activators to be used. For example, a metallocene compound having a ligand including cyclopentadienyl group and two sigma chloride ligands uses an aluminoxane as an activator. It was reported that the activity of the catalyst may increase when the chloride group of such metallocene compound is substituted with other ligands (for example, benzyl group or trimethylsilylmethyl group (—$CH_2SiMe_3$)).

European Patent No. 1462464 discloses a polymerization example using a hafnium metallocene compound including chloride, benzyl, and trimethylsilylmethyl groups. In addition, it was reported that the generation energy of activated species may vary according to the alkyl ligand combined to the center metal (J. Am. Chem. Soc. 2000, 122, 10358). Korean Patent No. 820542 discloses a catalyst for olefin polymerization having a quinoline-based ligand, and this patent relates to a catalyst having a leaving group including silicone or germanium atom in addition to methyl group.

Dow Co. had presented [$Me_2Si(Me_4C_5)NtBu$]$TiCl_2$ (Constrained-Geometry Catalyst, hereinafter 'CGC') in the early 1990's (U.S. Pat. No. 5,064,802), the superior aspects of the CGC to prior known metallocene catalysts in copolymerization reaction of ethylene and α-olefin can be largely summarized into two ways as follows: (1) it shows high activity even in high polymerization temperature and forms a polymer of high molecular weight, (2) the copolymerizing ability of α-olefin such as 1-hexene and 1-octene which have large steric hindrance is also very excellent. As various characteristics in the polymerization reaction of the CGC became gradually known, there have been many efforts to synthesize derivatives of the same for using it as a polymerization catalyst in the academic world and the industrial world.

As an approaching method, a synthesis of a metal compound to which various bridges and nitrogen substituents are introduced instead of silicone bridges and a polymerization using the same have been attempted. Representative metal compounds known up to recently include phosphorus, ethylene or propylene, methylidene, and methylene bridges respectively introduced thereto instead of silicone bridge of CGC structure, but they didn't show excellent results in the aspects of polymerization activity or copolymerization performance in comparison to CGC when they were applied to polymerization of ethylene or copolymerization of ethylene and alpha olefins.

As other approaching method, compounds including oxido ligands instead of amido ligands of the CGC have been largely synthesized and polymerizations using the same have been partially attempted.

However, very few catalysts have been being applied in practice in commercial factories among above attempts.

SUMMARY OF THE INVENTION

It is an aspect of the present invention to provide a novel ligand compound and a preparation method thereof for resolving the problems.

It is another aspect of the present invention to provide a transition metal compound including the ligand compound and a preparation method thereof.

In order to achieve the goals, the present invention provides the ligand compound represented by the following Chemical Formula 1:

[Chemical Formula 1]

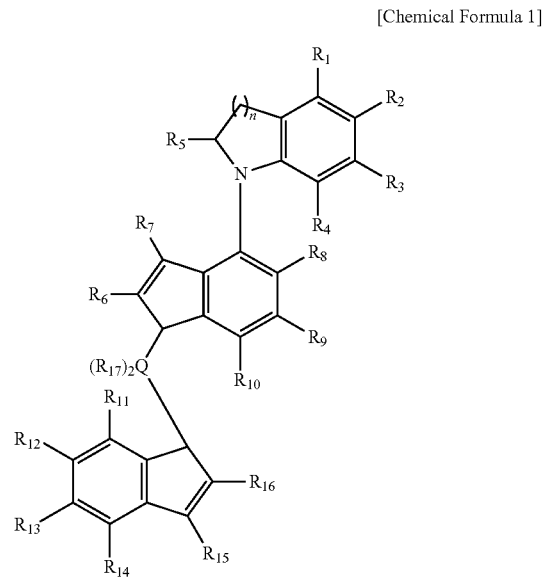

here, n is an integer of 1 to 2;

$R_1$ to $R_{16}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, a $C_3$-$C_{20}$ cycloalkyl, a $C_5$-$C_{20}$ heteroring, or silyl, and 2 or more adjacent groups among $R_1$ to $R_{16}$ may be connected together via an alkylidine group including a $C_1$-$C_{20}$ alkyl group or a $C_6$-$C_{20}$ aryl group to form a ring;

$R_{17}$ is hydrogen, a halogen, a $C_1$-$C_{20}$ alkyl, a $C_6$-$C_{20}$ aryl, or a $C_1$-$C_{20}$ alkoxy; and Q is carbon or silicon.

Furthermore, the present invention provides a preparation method of the ligand compound represented by the following Chemical Formula 1 including the step of carrying out the reaction of the compound represented by the following Chemical Formula 3 and the compound represented by the following Chemical Formula 4 or the lithium salt thereof:

[Chemical Formula 3]

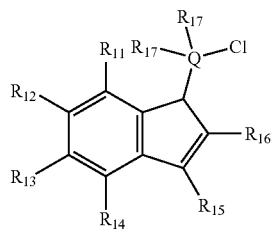

[Chemical Formula 4]

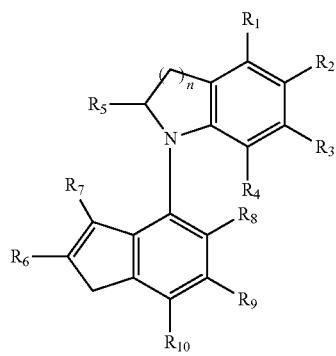

[Chemical Formula 1]

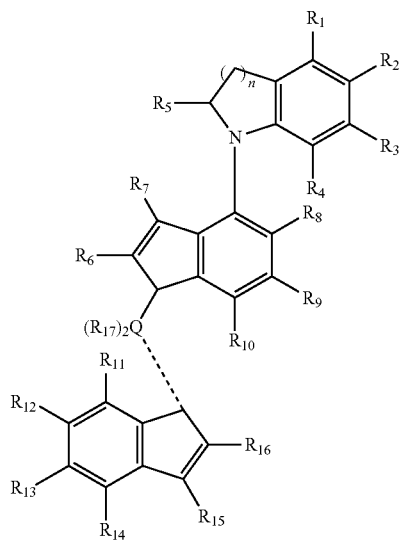

In Chemical Formulae 1, 3, and 4, $R_1$ to $R_{17}$, Q, and n are the same as defined in Chemical Formula 1.

Furthermore, the present invention provides the transition metal compound represented by the following Chemical Formula 2:

[Chemical Formula 2]

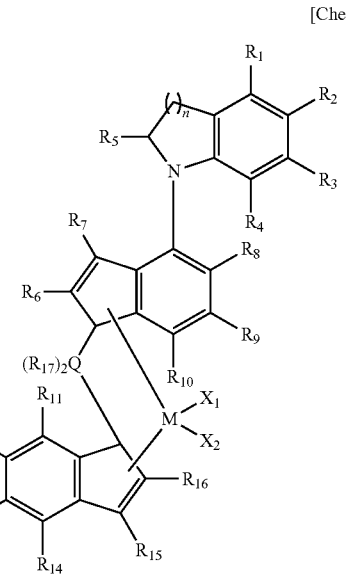

In Chemical Formula 2, $R_1$ to $R_{17}$, Q, and n are the same as defined in Chemical Formula 1;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

Furthermore, the present invention provides a preparation method of the transition metal compound represented by the following Chemical Formula 2 including the step of carrying out the reaction of the ligand compound represented by the following Chemical Formula 1 and the compound represented by the following Chemical Formula 9.

[Chemical Formula 1]

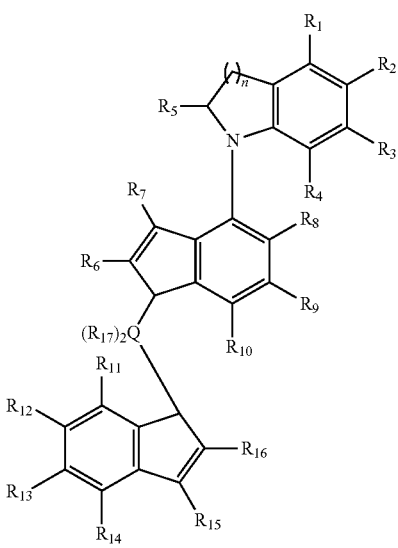

According to one aspect of the present invention, the ligand compound represented by the following Chemical Formula 1 is provided.

[Chemical Formula 1]

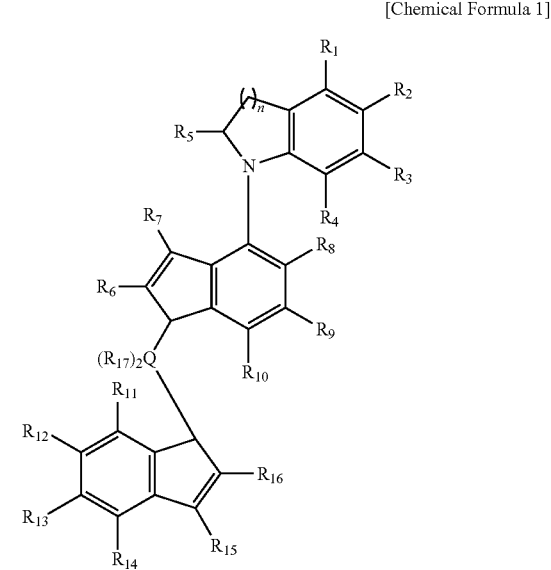

In Chemical Formula 1, n is an integer of 1 to 2;

$R_1$ to $R_{16}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, a $C_3$-$C_{20}$ cycloalkyl, a $C_5$-$C_{20}$ heteroring, or silyl, and 2 or more adjacent groups among $R_1$ to $R_{16}$ may be connected together via an alkylidine group including a $C_1$-$C_{20}$ alkyl group or a $C_6$-$C_{20}$ aryl group to form a ring;

$R_{17}$ is hydrogen, a halogen, a $C_1$-$C_{20}$ alkyl, a $C_6$-$C_{20}$ aryl, or a $C_1$-$C_{20}$ alkoxy; and Q is carbon or silicon.

Details of each substituent defined in Chemical Formulae 1 to 9 of the present invention are as follows.

The alkyl includes a linear or branched alkyl group.

The alkenyl includes a linear or branched alkenyl group.

According to one embodiment of the present invention, the aryl is preferably a $C_6$-$C_{20}$ aryl group and, specifically, it may be phenyl, naphthyl, anthracenyl, pyridyl, dimethylanilinyl, anisolyl, and so on, but it is not limited to or by them.

The alkylaryl means an aryl group substituted with the alkyl group.

The arylalkyl means an alkyl group substituted with the aryl group.

The halogen means fluorine, chlorine, bromine, or iodine.

The silyl may be trimethylsilyl, triethylsilyl, tripropylsilyl, tributylsilyl, trihexylsilyl, triisopropylsilyl, triisobutylsilyl, triethoxysilyl, triphenylsilyl, tris(trimethylsilyl)silyl, and so on, but it is not limited to or by them.

The aryl is preferably a $C_6$-$C_{20}$ aryl group and, specifically, may be phenyl, naphthyl, anthracenyl, pyridyl, dimethylanilinyl, anisolyl, and so on, but it is not limited to or by them.

The heteroring means a primary aliphatic or aromatic hydrocarbon group including $C_5$-$C_{20}$ ring atoms and one or more hetero atoms, and it may be a single ring or a condensed ring of 2 or more rings. And, the heteroring may $M(X_1X_2)_2$ [Chemical Formula 9]

[Chemical Formula 2]

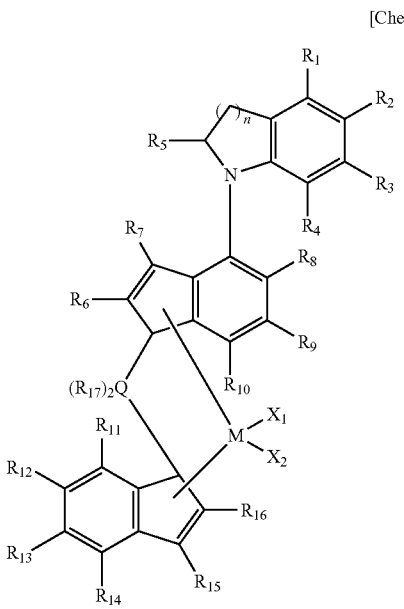

In Chemical Formulae 1, 2, and 9, $R_1$ to $R_{17}$, Q, and n are the same as defined in Chemical Formula 1;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

The novel ligand compound of the present invention and the transition metal compound including the same may be usefully used as a catalyst for a polymerization reaction in the preparation of an olefin-based polymer.

DETAILED DESCRIPTION OF THE EMBODIMENTS

The terms used in this description are just for explaining exemplary examples and it is not intended to restrict the present invention. The singular expression may include the plural expression unless it is differently expressed contextually. It must be understood that the terms such as "include", "equip", and "have" in the present description are only used for designating the existence of characteristics taken effect, numbers, steps, components, or combinations thereof, and do not exclude the existence or the possibility of addition of one or more different characteristics, numbers, steps, components of combinations thereof beforehand.

The present invention can be variously modified and have various examples, and specific examples of the present invention are explained in this description. However, it is not intended to limit the present invention to the specific examples and it must be understood that the present invention includes every modifications, equivalents, or replacements included in the idea and technical scope of the present invention.

Hereinafter, the present invention is explained in more detail.

be substituted with an alkyl group or not. For example, it may be indoline, tetrahydroquinoline, and so on, but it is not limited to or by them.

According to one embodiment of the present invention, $R_1$ to $R_{16}$ may be independently hydrogen, a $C_1$-$C_{20}$ alkyl, a $C_6$-$C_{20}$ aryl, a $C_7$-$C_{20}$ alkylaryl, a $C_7$-$C_{20}$ arylalkyl, or a $C_5$-$C_{20}$ heteroring, and $R_{17}$ may be a $C_1$-$C_{20}$ alkyl or a $C_6$-$C_{20}$ aryl.

The ligand compound represented by Chemical Formula 1 has a structure in which bisindenyl groups are crosslinked by Q (carbon or silicon), and any one indenyl group is connected to indoline group or tetrahydroquinoline group so as to show C1-asymmetric crosslinking structure.

According to one embodiment of the present invention, the ligand compound represented by Chemical Formula 1 may be represented by any one of the following structural formulae but it is not limited to or by them.

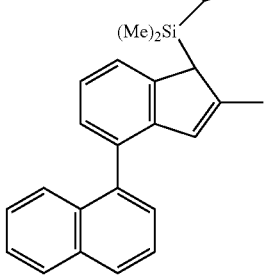

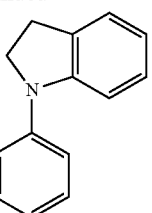
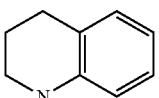
-continued
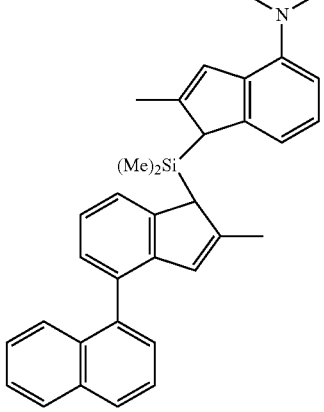

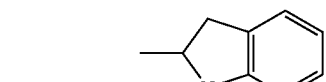
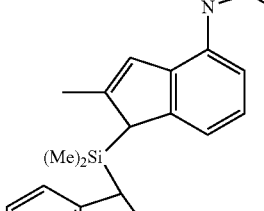

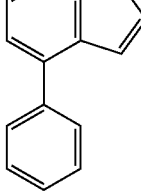

-continued
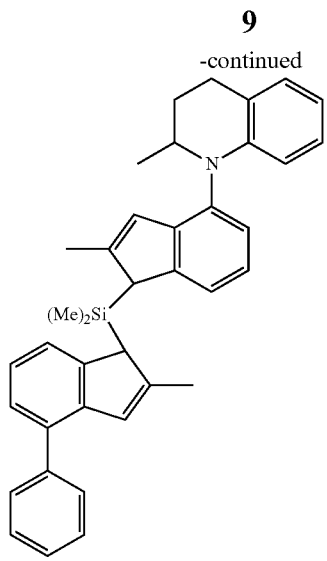
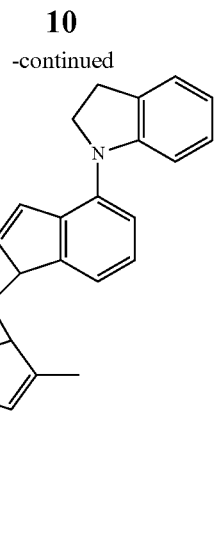
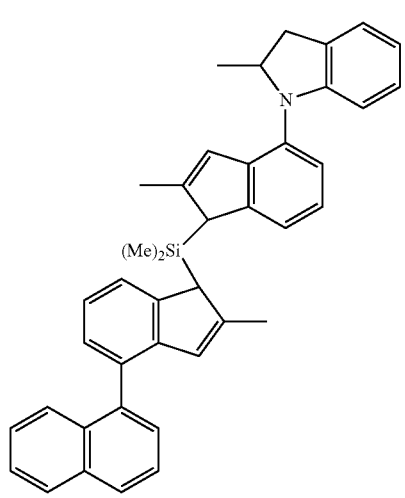
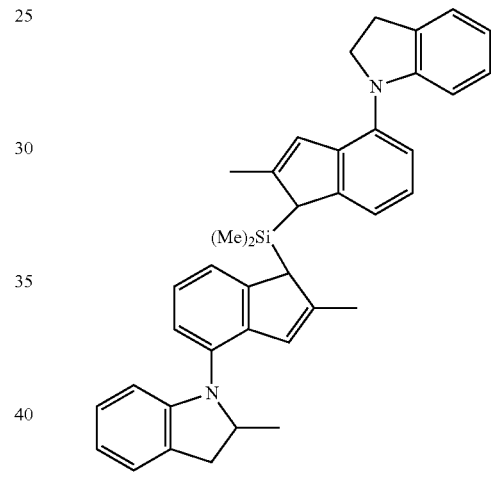
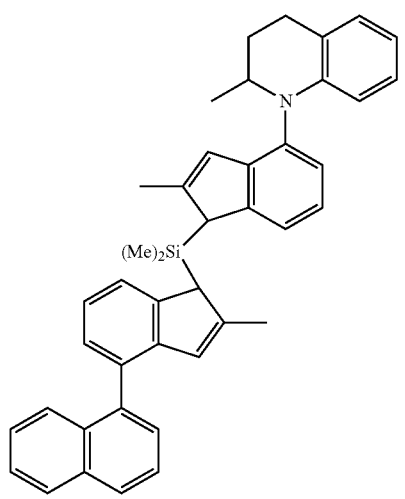
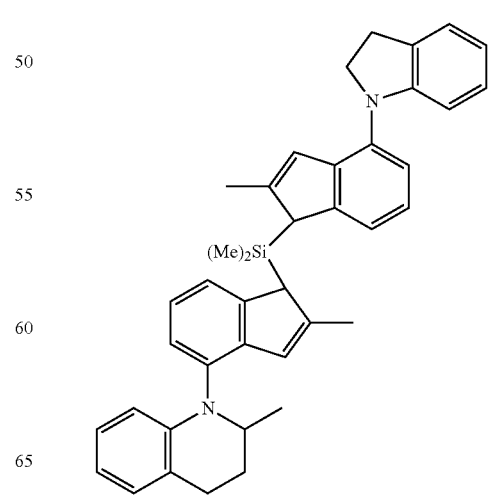

11
-continued
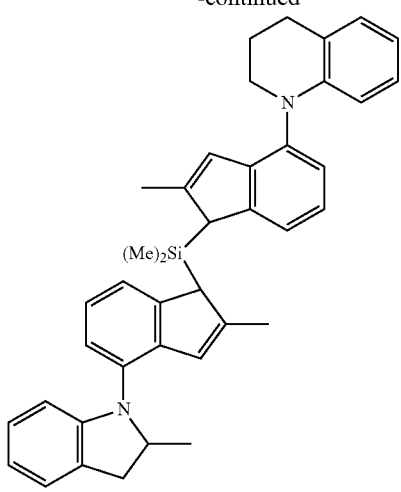
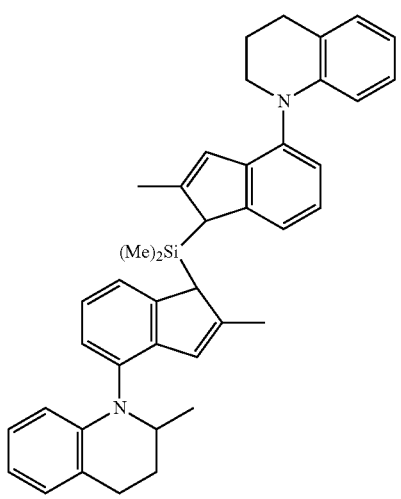
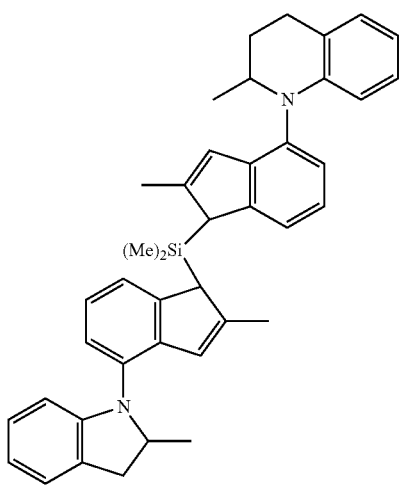
12
-continued
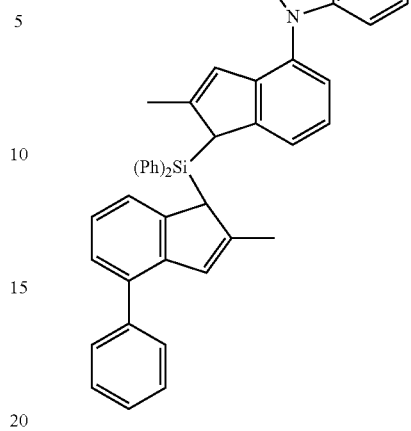
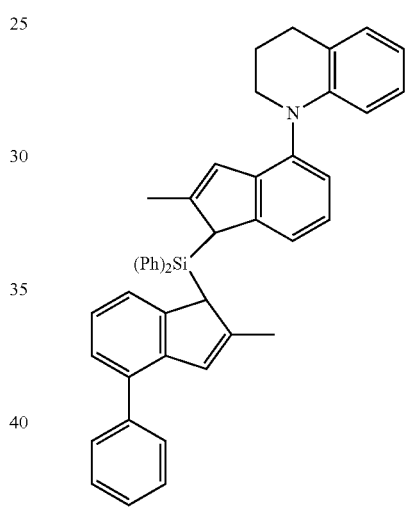
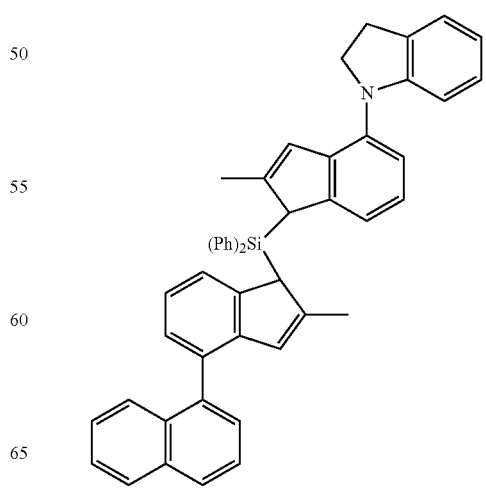

13
-continued
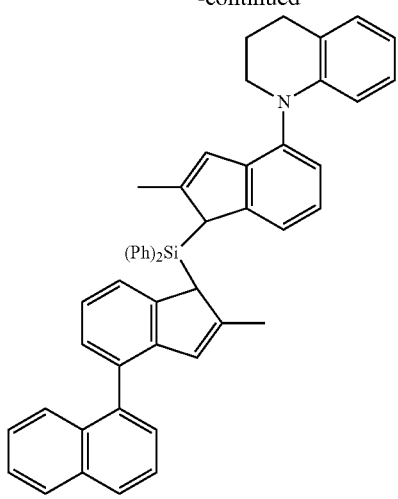
14
-continued
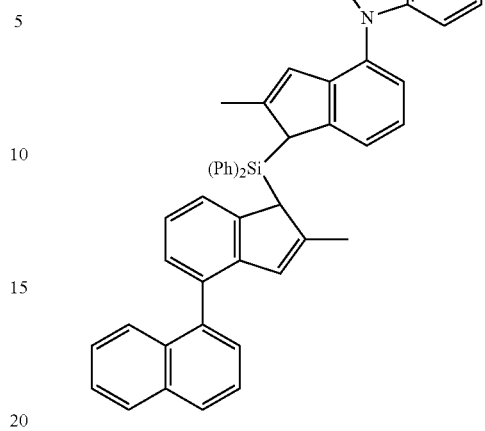
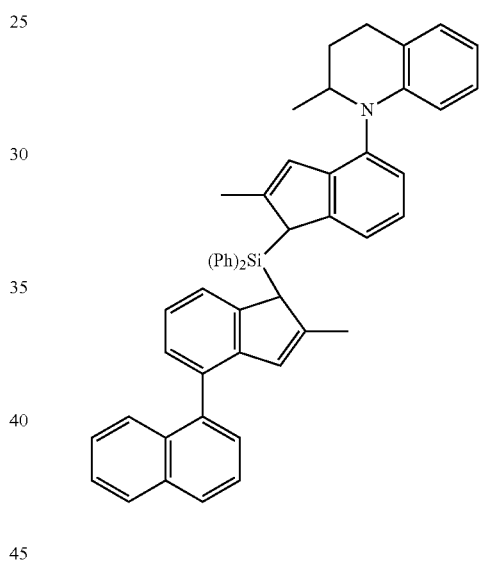
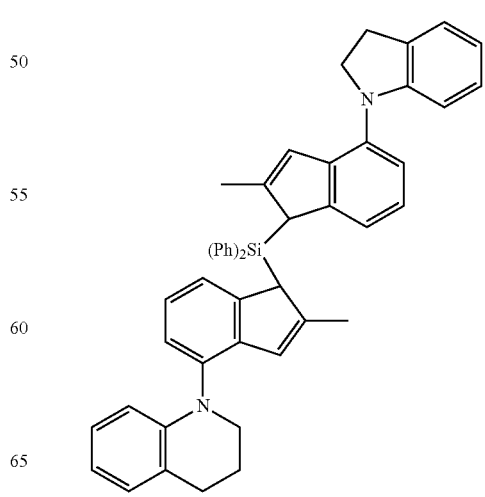

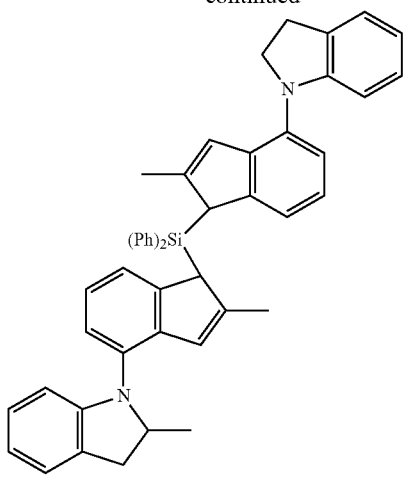

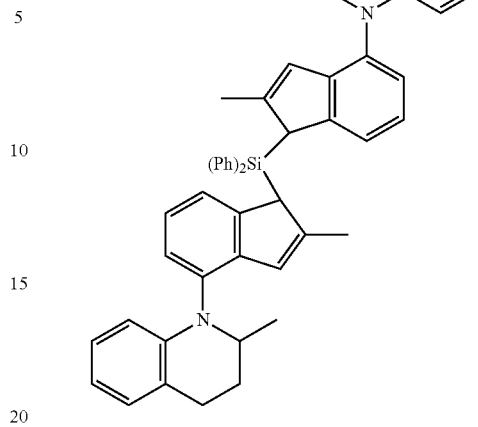

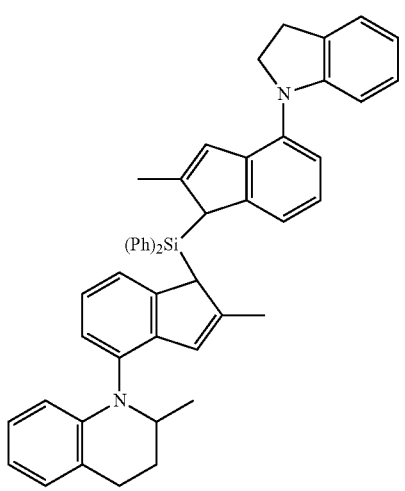

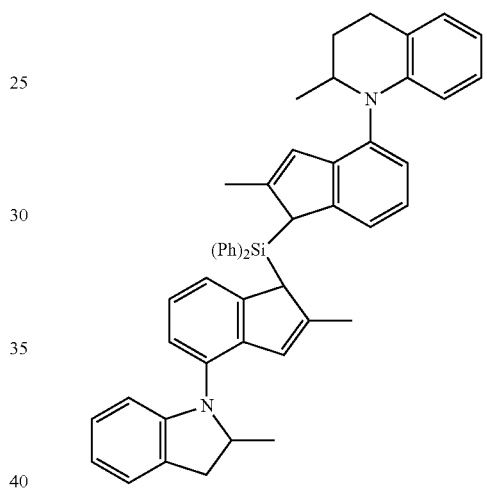

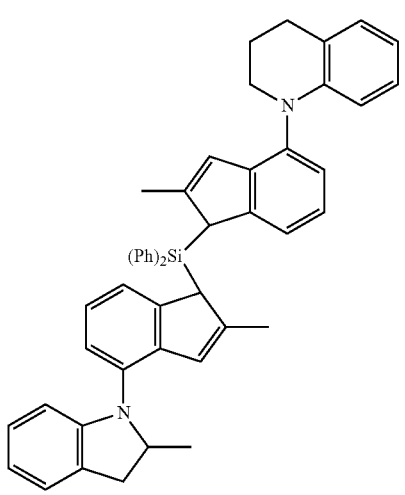

In structural formulae, Me means methyl group and Ph means phenyl group.

The compound represented by Chemical Formula 1 may be a ligand compound which can form a chelate with a metal.

Furthermore, according to another aspect of the present invention, a preparation method of the ligand compound represented by the following Chemical Formula 1 including the step of carrying out the reaction of the compound represented by the following Chemical Formula 3 and the compound represented by the following Chemical Formula 4 or the lithium salt thereof is provided.

[Chemical Formula 3]

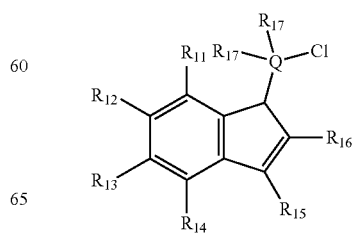

-continued

[Chemical Formula 4]

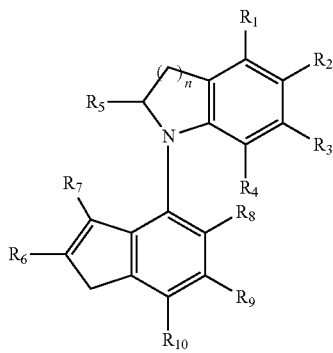

[Chemical Formula 1]

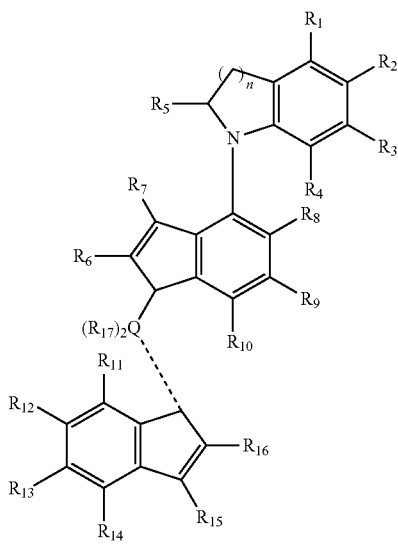

In Chemical Formulae 1, 3, and 4, n is an integer of 1 to 2;

$R_1$ to $R_{16}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, a $C_3$-$C_{20}$ cycloalkyl, a $C_5$-$C_{20}$ heteroring, or silyl, and 2 or more adjacent groups among $R_1$ to $R_{16}$ may be connected together via an alkylidine group including a $C_1$-$C_{20}$ alkyl group or a $C_6$-$C_{20}$ aryl group to form a ring;

$R_{17}$ is hydrogen, a halogen, a $C_1$-$C_{20}$ alkyl, a $C_6$-$C_{20}$ aryl, or a $C_1$-$C_{20}$ alkoxy; and Q is carbon or silicon.

In the preparation method of the ligand compound, the compound represented by Chemical Formula 1 is prepared by the reaction of the compound represented by Chemical Formula 3 and the compound represented by Chemical Formula 4 or the lithium salt thereof.

More specifically, according to one embodiment of the present invention, the lithium salt of the compound represented by Chemical Formula 4 is prepared by the reaction of the compound represented by Chemical Formula 4 and an organic lithium compound such as n-BuLi. After mixing the lithium salt with the compound represented by Chemical Formula 3, the ligand compound represented by Chemical Formula 1 may be obtained by carrying out the reaction of the mixture in the presence of ether and CuCN.

At this time, the compound represented by Chemical Formula 3 may be obtained by the reaction of the compound represented by Chemical Formula 5 or the lithium salt thereof and the compound represented by Chemical Formula 6. More specifically, the lithium salt of the compound represented by Chemical Formula 5 is prepared by the reaction of the compound represented by Chemical Formula 5 and an organic lithium compound such as n-BuLi. After mixing the lithium salt with the compound represented by Chemical Formula 6, the compound represented by Chemical Formula 3 may be obtained by carrying out the reaction of the mixture with stirring.

[Chemical Formula 5]

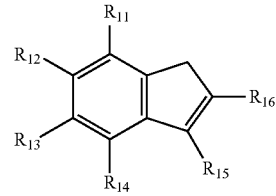

$(R_{17})_2QCl_2$   [Chemical Formula 6]

Furthermore, the compound represented by Chemical Formula 4 may be prepared by carrying out the coupling reaction of the indenyl halide compound represented by Chemical Formula 7 and the derivative compound of indoline or tetrahydroquinoline represented by Chemical Formula 8 in the presence of a base or a palladium catalyst to form C—N bond. At this time, the palladium catalyst is not limited particularly and, for example, it may be bis(tri(tert-butyl)phosphine))palladium (((tert-Bu)$_3$P)$_2$Pd), tetrakis(triphenylphosphine)palladium (Pd(PPh$_3$)$_4$), palladium chloride (PdCl$_2$), palladium acetate (Pd(OAc)$_2$), bis(dibenzylideneacetone)palladium (Pd(dba)$_2$), and the like.

[Chemical Formula 7]

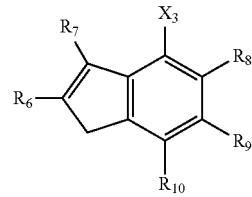

[Chemical Formula 8]

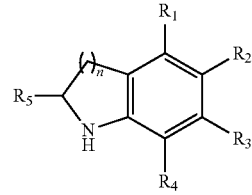

In Chemical Formulae 3 to 8, $R_1$ to $R_{17}$, Q, and n are the same as defined in Chemical Formula 1, and $X_3$ is a halogen.

According to the preparation method of the present invention, the ligand compound represented by Chemical Formula 1 may be obtained as any one form of racemic body or meso compound, or a mixture of the racemic body and the meso compound.

Furthermore, according to another aspect of the present invention, the transition metal compound represented by Chemical Formula 2 is provided. The transition metal compound of the present invention has the structure in which a Group 4 transition metal is combined with the ligand compound represented by Chemical Formula 1 by coordinate bond, and it may be represented by the following Chemical Formula 2.

[Chemical Formula 2]

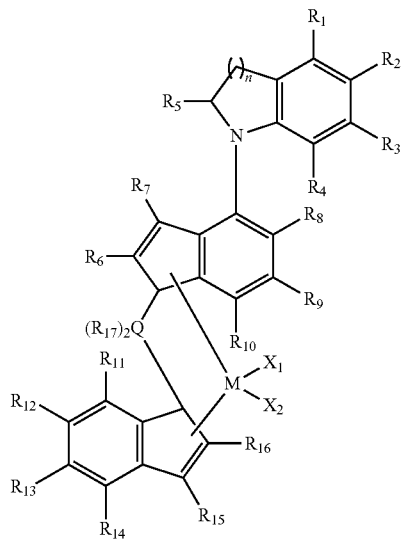

In Chemical Formula 2, n is an integer of 1 to 2;

$R_1$ to $R_{16}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, a $C_3$-$C_{20}$ cycloalkyl, a $C_5$-$C_{20}$ heteroring, or silyl, and 2 or more adjacent groups among $R_1$ to $R_{16}$ may be connected together via an alkylidine group including a $C_1$-$C_{20}$ alkyl group or a $C_6$-$C_{20}$ aryl group to form a ring;

$R_{17}$ is hydrogen, a halogen, a $C_1$-$C_{20}$ alkyl, a $C_6$-$C_{20}$ aryl, or a $C_1$-$C_{20}$ alkoxy;

Q is carbon or silicon;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

According to one embodiment of the present invention, $R_1$ to $R_{16}$ may be independently hydrogen, a $C_1$-$C_{20}$ alkyl, a $C_6$-$C_{20}$ aryl, a $C_7$-$C_{20}$ alkylaryl, a $C_7$-$C_{20}$ arylalkyl, or a $C_5$-$C_{20}$ heteroring, and $R_{17}$ may be a $C_1$-$C_{20}$ alkyl or a $C_6$-$C_{20}$ aryl.

According to one embodiment of the present invention, the Group 4 transition metal corresponding to M may be Ti, Zr, Hf, and so on but it is not limited to or by them.

Furthermore, according to one embodiment of the present invention, the transition metal compound represented by Chemical Formula 2 may be represented by any one of the following structural formulae but it is not limited to or by them.

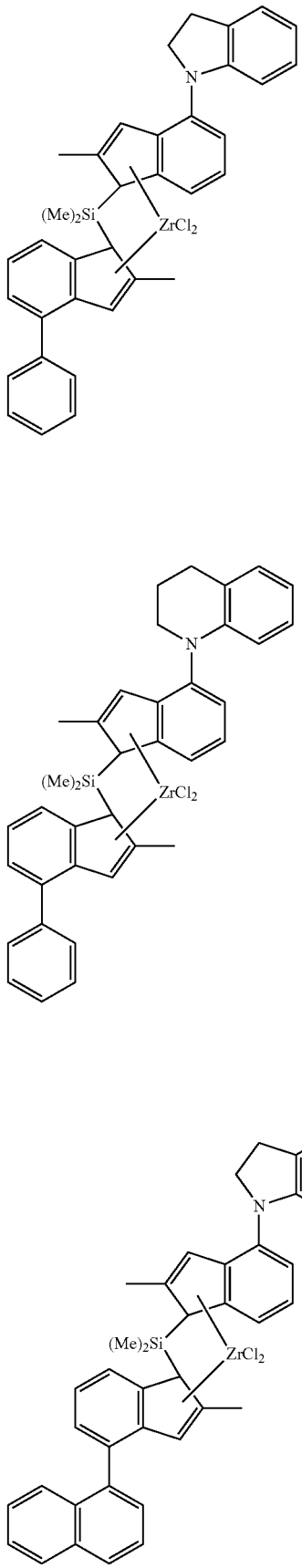

-continued
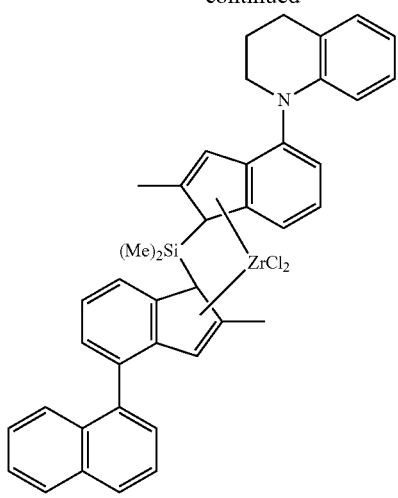
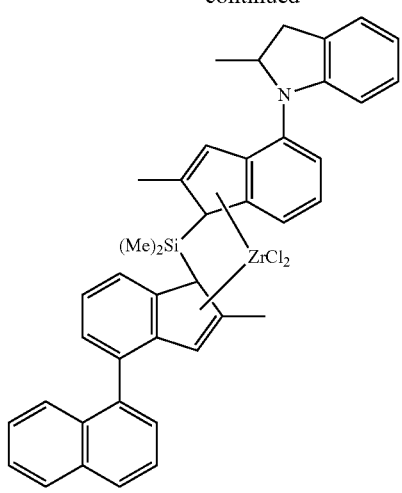
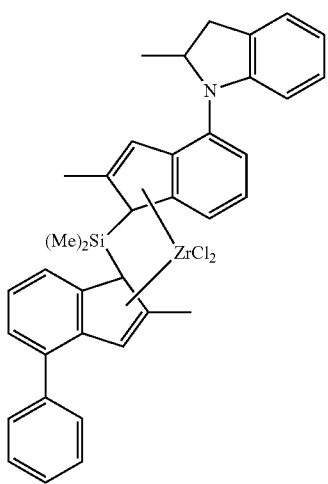
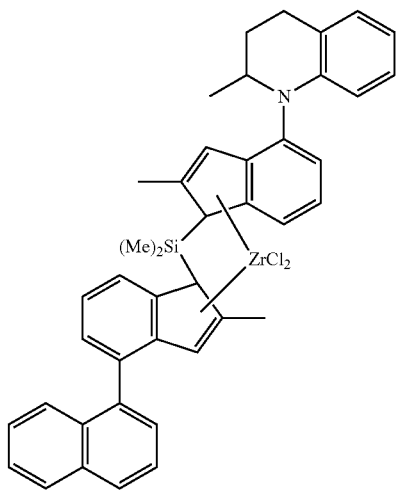
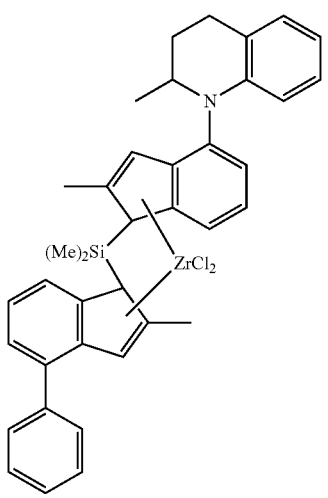
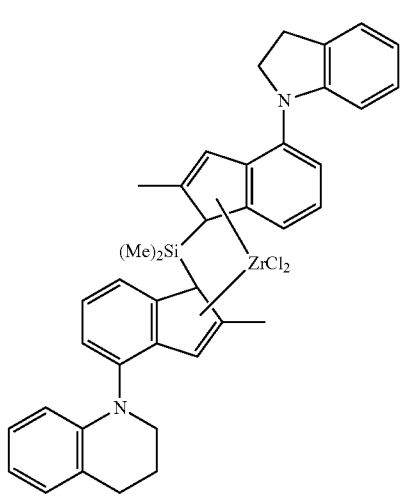

23
-continued
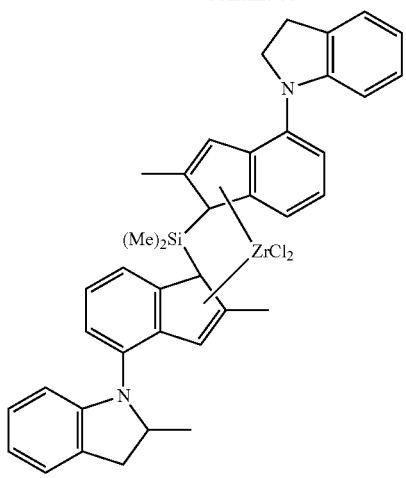
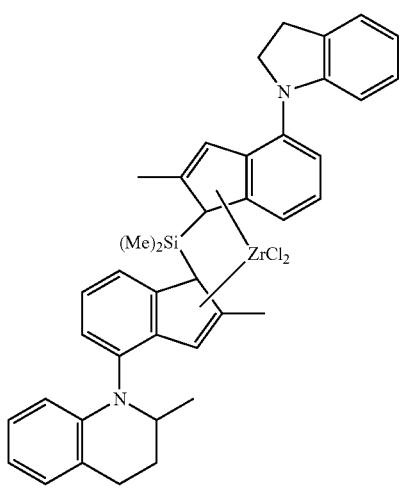
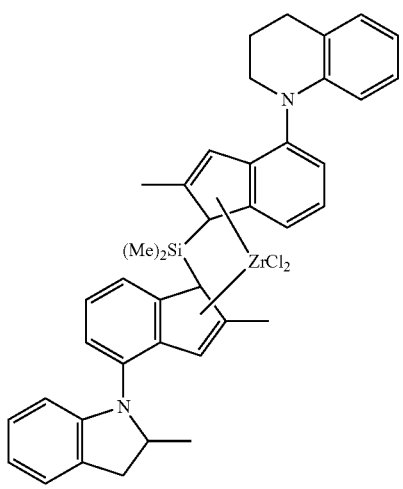
24
-continued
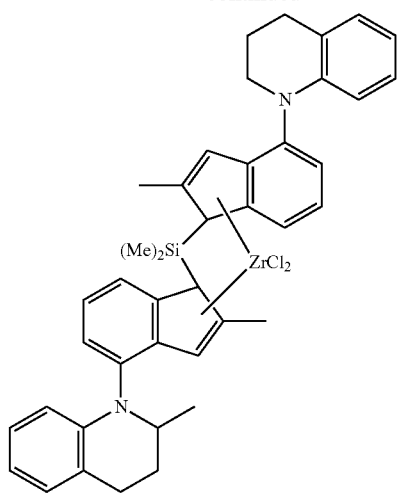
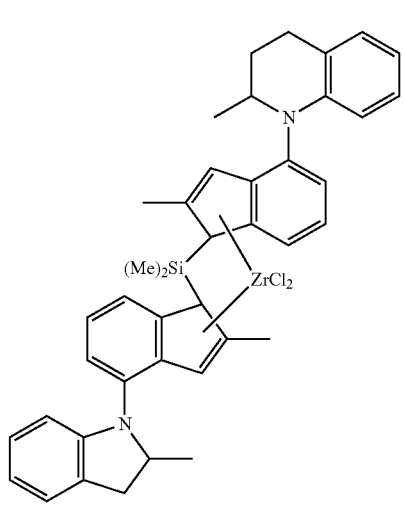
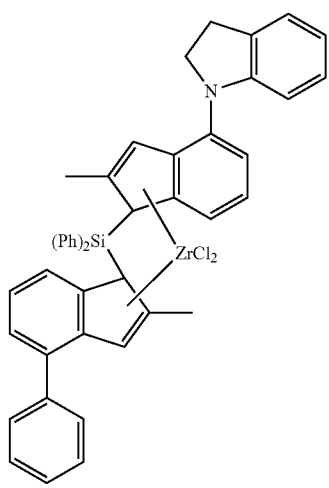

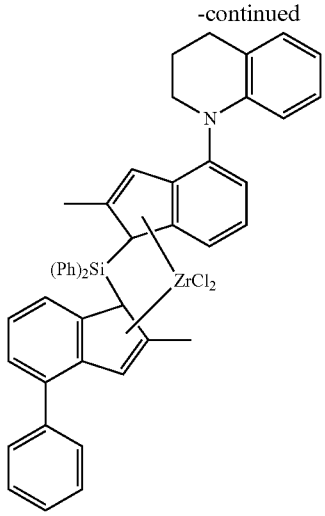
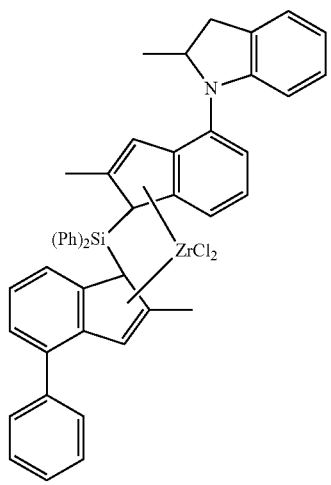
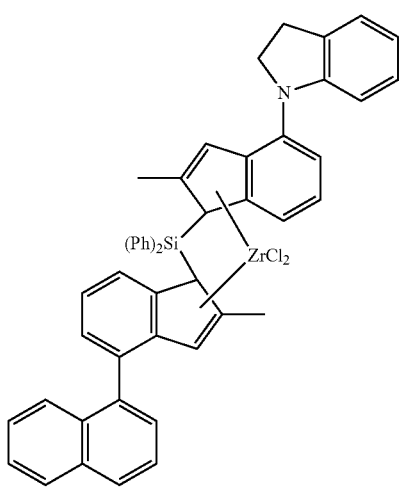
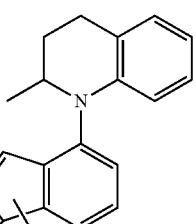
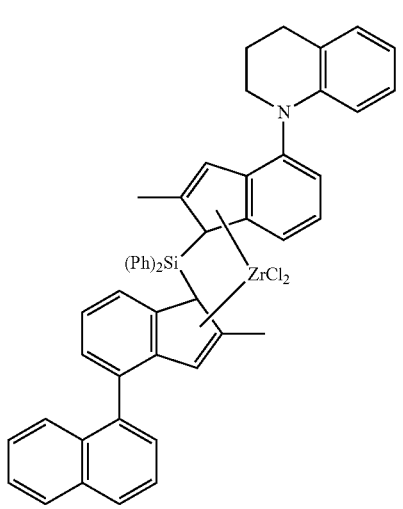
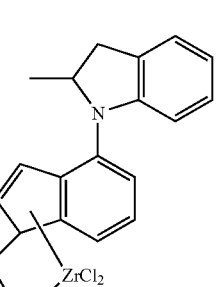

27
-continued
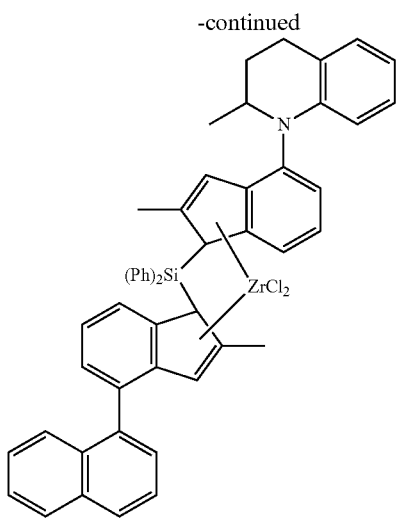
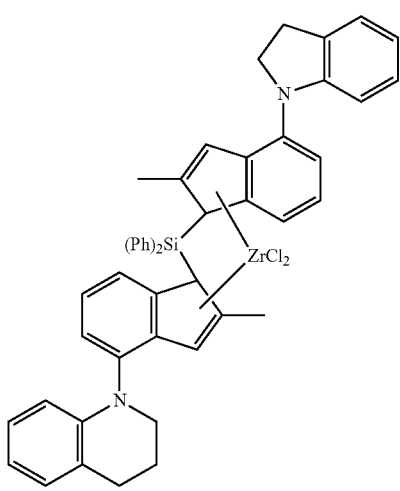
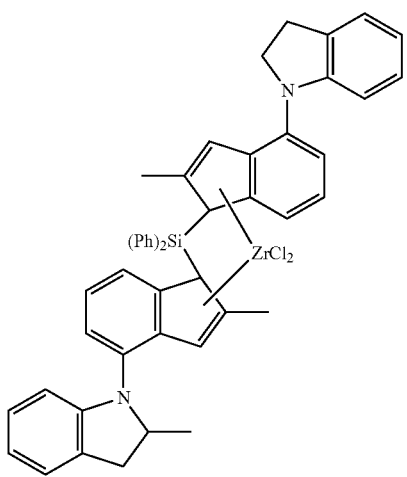
28
-continued
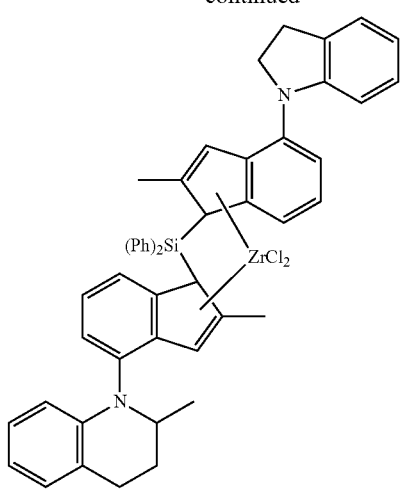
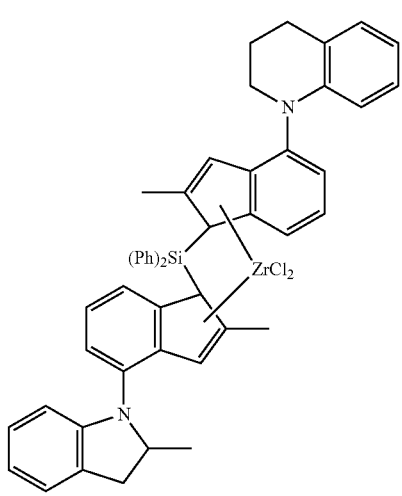
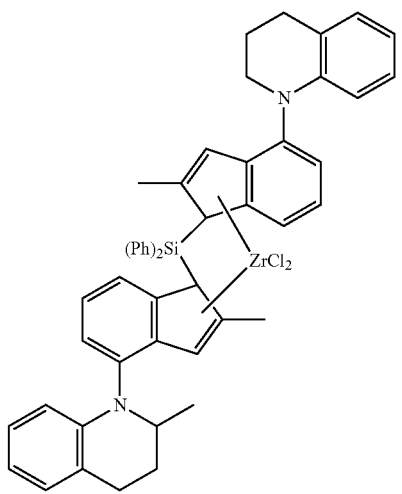

29
-continued
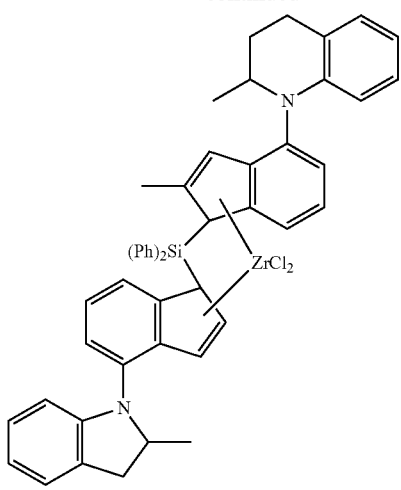
30
-continued
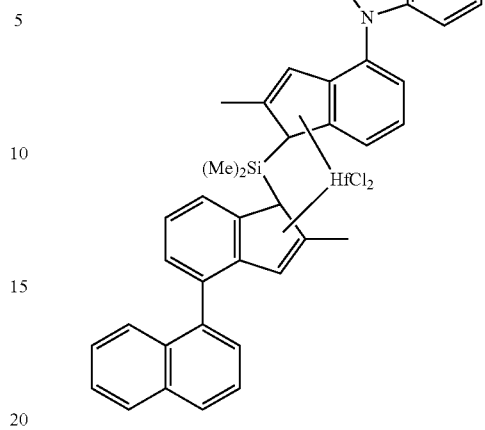
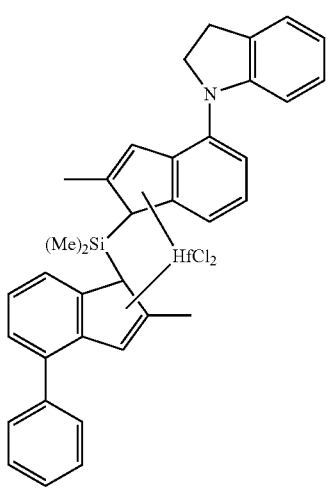
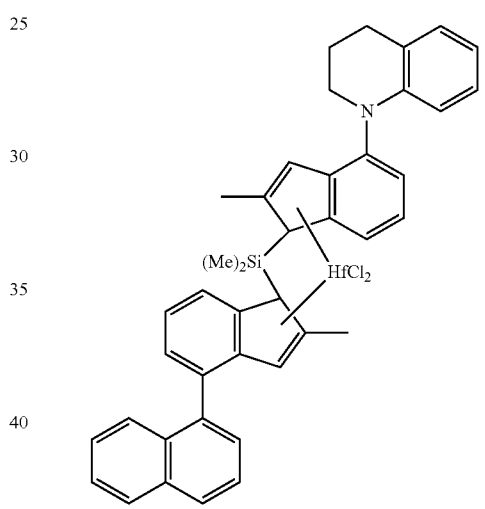
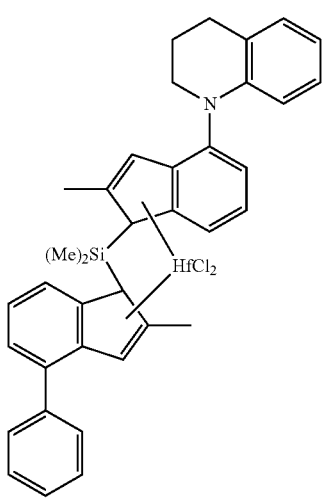
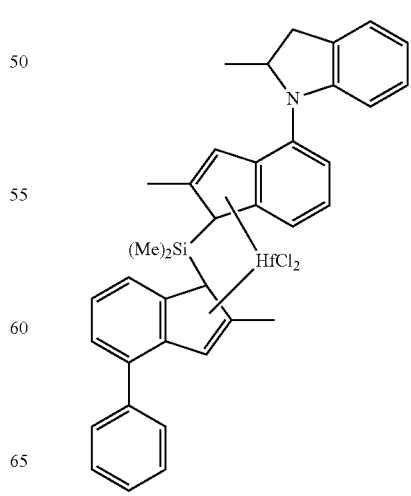

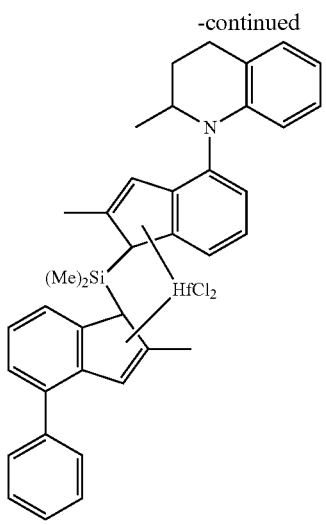
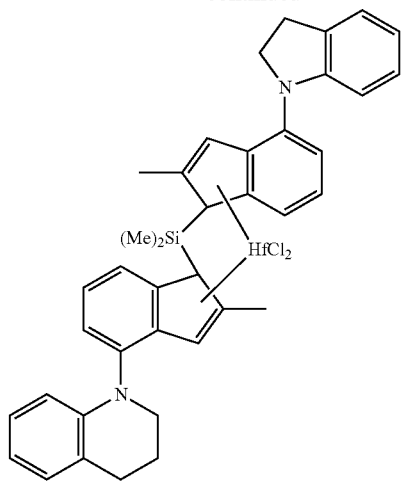
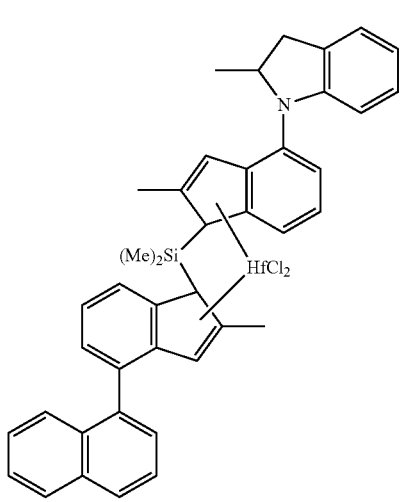
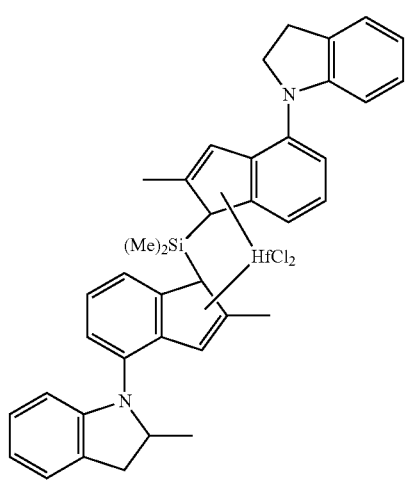
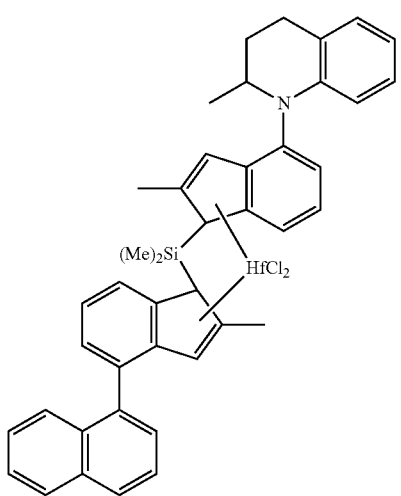
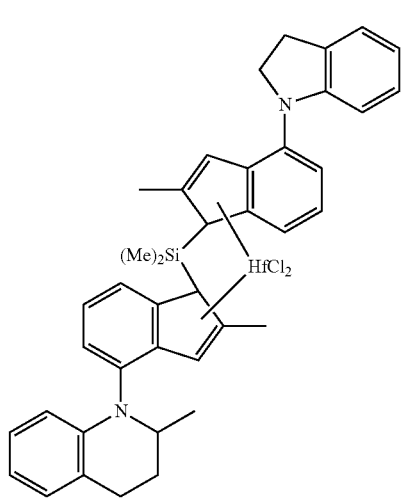

33
-continued
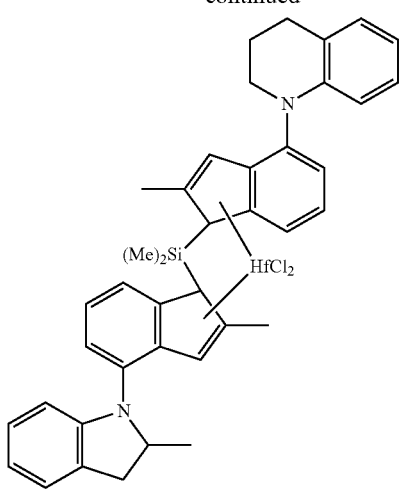
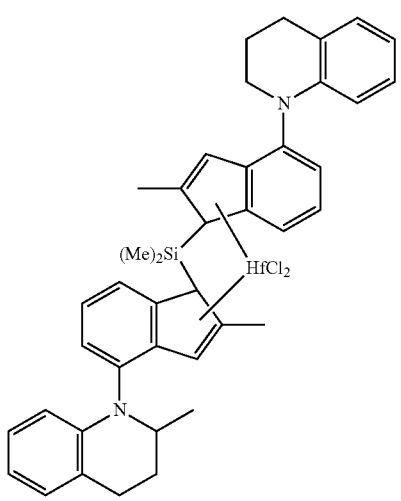
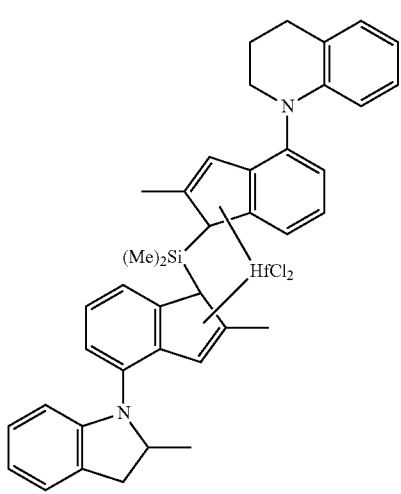
34
-continued
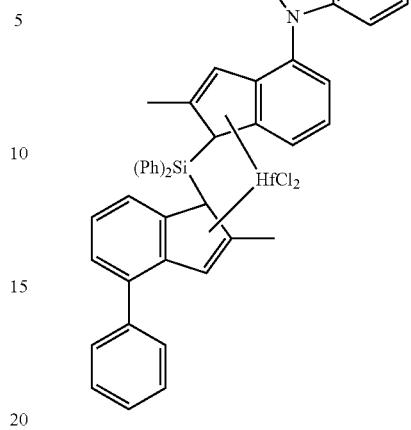
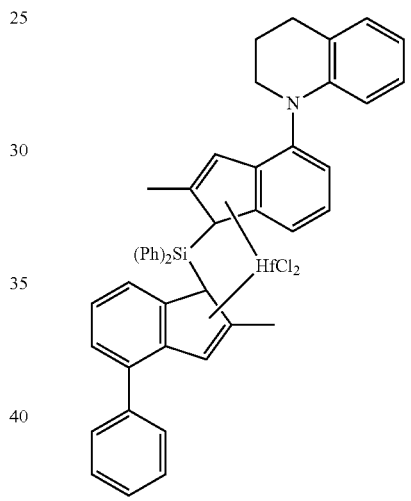
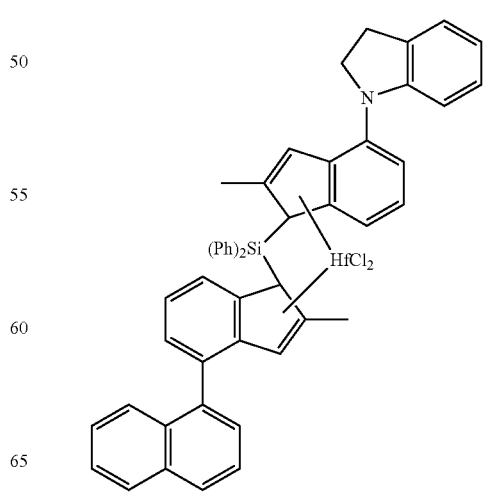

35
-continued
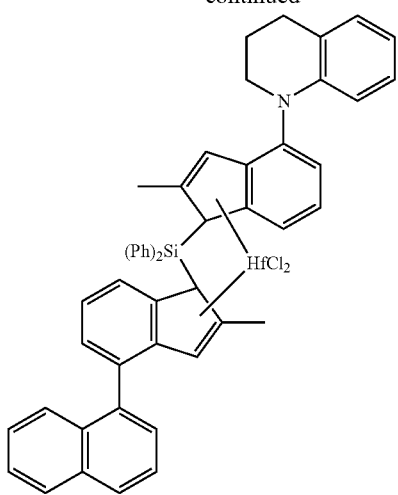
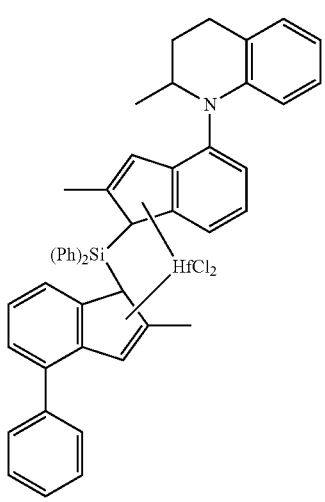
36
-continued
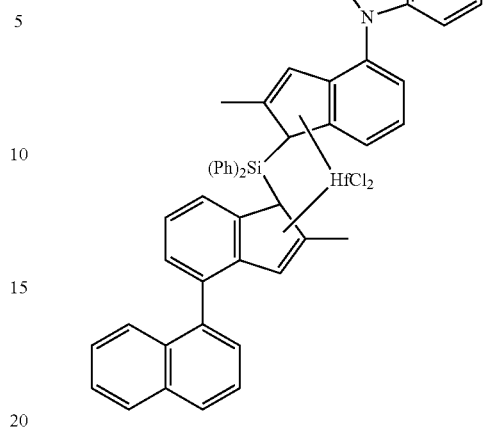
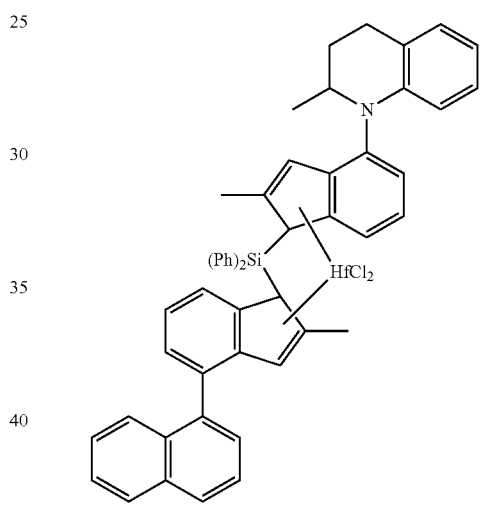

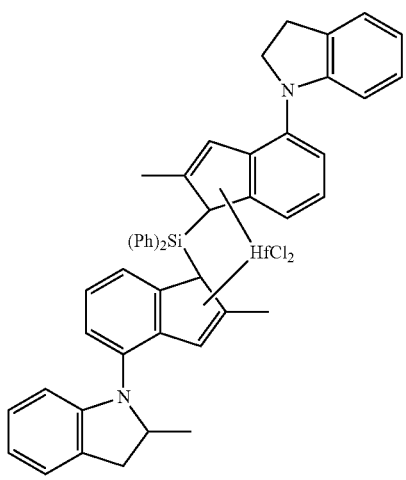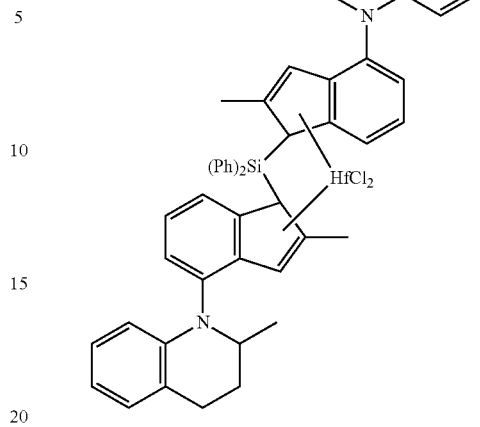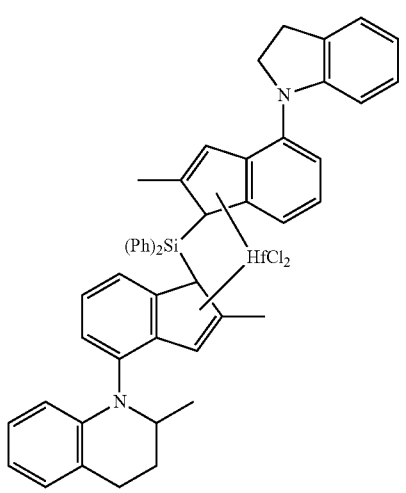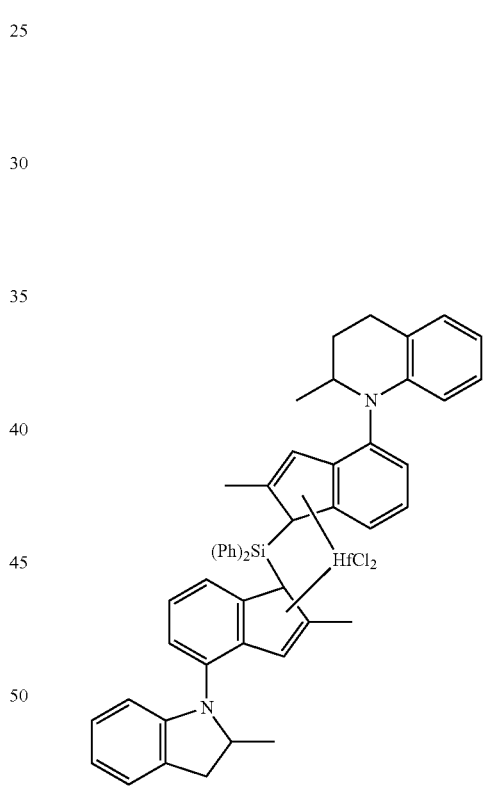

In the structural formulae, Me means methyl group and Ph means phenyl group.

Furthermore, according to another aspect of the present invention, a preparation method of the transition metal compound represented by Chemical Formula 2 is provided.

The preparation method of the transition metal compound according to another aspect of the present invention includes the step of carrying out the reaction of the ligand compound represented by the following Chemical Formula 1 and the compound represented by the following Chemical Formula 9.

[Chemical Formula 1]

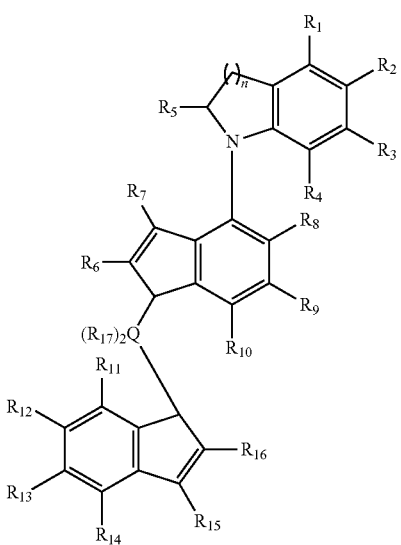

M(X₁X₂)₂ [Chemical Formula 9]

[Chemical Formula 2]

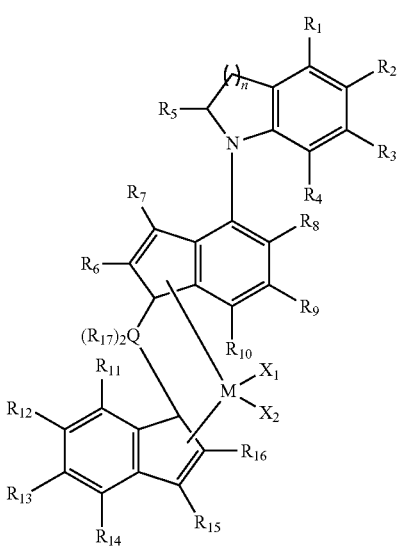

In the Chemical Formulae 1, 2, and 9, n is an integer of 1 to 2;

$R_1$ to $R_{16}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, a $C_3$-$C_{20}$ cycloalkyl, a $C_5$-$C_{20}$ heterforing, or silyl, and 2 or more adjacent groups among $R_1$ to $R_{16}$ may be connected together via an alkylidine group including a $C_1$-$C_{20}$ alkyl group or a $C_6$-$C_{20}$ aryl group to form a ring;

$R_{17}$ is hydrogen, a halogen, a $C_1$-$C_{20}$ alkyl, a $C_6$-$C_{20}$ aryl, or a $C_1$-$C_{20}$ alkoxy;

Q is carbon or silicon;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

According to one embodiment of the present invention, the Group 4 transition metal corresponding to M may be Ti, Zr, Hf, and so on but it is not limited to or by them.

More specifically, at first, the ligand compound represented by Chemical Formula 1 is made into the lithium salt thereof by the reaction with an organic lithium compound such as n-BuLi. The lithium salt is mixed with the metal source represented by Chemical Formula 9 and the mixture is stirred to react. The reaction product is filtered and the precipitate is obtained. And then, the organic metal compound represented by Chemical Formula 2 having the complex form in which a metal atom is combined with the ligand compound is obtained by washing the precipitate and drying the same under decompression.

According to the preparation method of the present invention, the transition metal compound represented by Chemical Formula 2 may be obtained respectively as any one of racemic body or meso compound, or a mixture of the racemic body and the meso compound. When the compound is a mixture of the racemic body and the meso compound, it is possible to obtain only the racemic body of the transition metal compound finally through a recrystallization step.

The ligand compound represented by Chemical Formula 1 and the transition metal compound represented by Chemical Formula 2 have a structure in which bisindenyl groups are crosslinked by carbon or silicon, and each indenyl group is connected to indoline group or tetrahydroquinoline group so as to show C1-asymmetric crosslinking structure. Since the transition metal compound of the present invention includes indoline group or tetrahydroquinoline group which is plenty of electrons as disclosed above, electron density of the center metal of the same increases, the stability at high temperature thereof is high, and it can be usefully used to synthesize polyolefin polymers of high molecular weight, particularly, isotatic polyolefin polymers, for example, isotatic polypropylene.

The ligand compound of novel structure according to the present invention and the transition metal compound including the same may be used as a polymerization reaction catalyst for preparing olefin polymers.

Hereinafter, preferable examples and comparative examples are presented for understanding the present invention. However, the following examples are only for illustrating the present invention and the present invention is not limited to or by them.

EXAMPLES

In the following Examples, term "overnight" or "through the night" means about 12 to 16 hrs and term "room temperature" means the temperature of about 20 to 30° C. Organic reagents and solvents were purchased from Aldrich Co., Ltd. and Merck Co., Ltd. and refined by a standard method before use. In every steps of the syntheses, contact with air or moisture was cut off for increasing repeatability of experimental. NMR spectrum was obtained by using a 500 MHz NMR spectrometer for confirming the structure of the produced compound.

Synthesis of Ligand Compound and Transition Metal Compound

Example 1

Example 1-1: Synthesis of 1-(2-methyl-1H-inden-4-yl)-1,2,3,4-tetrahydroquinole

After putting 4-bromo-2-methyl-1H-indene (10 g, 47.83 mmol) in a 500 mL 2-neck Schlenk flask, LiOtBu (11.49 g, 143.49 mmol) was weighed in a glove box and tetrahydroquinone (6.244 mL, 49.74 mmol) was put in the flask. The palladium catalyst Pd(P(tBu)$_3$)$_2$ (0.049 g, 0.096 mmol) in another 100 mL Schlenk flask was weighed in a glove box. After transferring the palladium catalyst to the flask in which tetrahydroquinone was, the reaction was carried out at 110° C. for 4 hrs 30 mins and worked up. The reaction product was quenched by putting water in the flask and extracted with methylene chloride (MC), and then water was eliminated therefrom with Na$_2$SO$_4$ and the rest was vacuum dried. The compound of orange color (10.5 g, 84% yield) was obtained.

$^1$H-NMR (CDCl$_3$): δ 7.41~7.36 (m, 3H in isomers), 7.27~7.16 (m, 8H in isomers), 6.98 (t, 3H in isomers), 6.74 (m, 3H in isomers), 6.61 (m, 2H in isomers), 6.44 (s, 1H in isomers). 6.43 (d, 1H in isomers), 6.38 (d, 1H in isomers), 3.74~3.72 (m, 6H in isomers), 3.46 (s, 3H in isomers), 3.24 (s, 3H in isomers), 3.04~3.02 (m, 6H in isomers), 2.32~2.22 (m, 15H in isomers).

Example 1-2: Synthesis of chloro(2-methyl-4-phenyl-1H-inden-1-yl) dimethyl silane n-BuLi (2.5 M in n-Hx) (1.1 eq, 9.38 mL) was slowly added to 2-methyl-4-phenylindene (4.4 g, 21.3 mmol) and diethyl ether (100 mL) dropwise at −78° C., and the reaction of the mixture was carried out at room temperature through the night. After the reaction, the lithium salt was obtained by vacuum drying the product and filtering the same with hexane. After dispersing the obtained lithium salt in hexane again and adding (CH$_3$)$_2$SiCl$_2$ (dichlorodimethyl silane) (10 eq, 27.5 mL in hexane) thereto dropwise at −78° C., the reaction of the mixture was carried out at room temperature through the night. The compound of light yellow solid form was obtained with the yield of 93% by line-filtering and vacuum drying the reaction product.

$^1$H-NMR (CDCl$_3$): δ 7.28 (d, 2H), 7.22~7.21 (m, 3H), 7.13 (t, 1H), 7.06 (d, 1H), 6.96 (t, 1H), 6.56 (s, 1H), 3.43 (s, 1H), 2.04 (s, 3H), 0.205 (s, 3H), −0.033 (s, 3H).

Example 1-3: Synthesis of (4-(3,4-dihydroquinolin-1(2H)-yl)-2-methyl-1H-inden-1-yl)(4-phenyl-2-methyl-1H-inden-1-yl) dimethyl silane After putting 1-(2-methyl-1H-inden-4-yl)-1,2,3,4-tetrahydroquinole (2.2 g, 8.42 mmol) in a 100 mL Schlenk flask and dissolving the starting material by adding 40 mL of dry diethyl ether thereto, n-BuLi (2.5 M in n-Hx) (3.7 mL) was added thereto at −78° C. and the mixture was stirred at room temperature through the night. And then, the mixture was filtered by using a glass frit (G4). The remaining solid on the glass frit was vacuum dried and the lithiated product (2.2 g, 98% yield) of white solid was obtained. After putting the lithiated product (2.2 g, 8.03 mmol), chloro(2-methyl-4-phenyl-1H-inden-1-yl) dimethyl silane (2.40 g, 8.03 mmol), and copper cyanide (0.026 g, 0.29 mmol) in a 250 mL Schlenk flask in a glove box, 80 mL of dry diethyl ether was added thereto at −78° C. and the mixture was stirred at room temperature through the night. The reaction was terminated by adding 100 mL of aqueous NH$_4$Cl and 100 mL of deionized water after the reaction.

After separating the organic layer from water layer, the ligand compound of light yellowish solid (4.20 g, quantitative yield compared to the lithiated product, 99% yield compared to the starting material) was obtained by drying the organic layer with MgSO$_4$ and filtering and vacuum drying the same. As the result of $^1$H-NMR analysis, the ratio of rac:meso was about 1:1.

$^1$H-NMR (CDCl$_3$): δ 7.55~7.12 (m, 22H in rac- and meso-isomers), 7.04 (dd, 2H in rac- and meso-isomers), 6.85~6.80 (m, 4H in rac- and meso-isomers), 6.63 (td, 2H in rac- and meso-isomers), 6.47 (s, 2H in rac- and meso-isomers), 6.29 (d, 2H in rac- and meso-isomers), 3.81 (s, 2H in rac-isomer), 3.80 (s, 2H in meso-isomer), 3.70~3.59 (m, 4H in rac- and meso-isomers), 2.94 (t, 4H in rac- and meso-isomers), 2.27 (d, 2H in rac- and meso-isomers), 2.20 (d, 6H in meso-isomer), 2.18 (d, 6H in rac-isomer), 2.13~2.08 (m, 8H in rac- and meso-isomers), −0.22 (s, 3H in meso-isomer), 0.23 (d, 6H in rac-isomer), −0.25 (s, 3H in meso-isomer).

Example 1-4: Synthesis of rac-dimethylsilylene-(4-(3,4-dihydroquinolin-1(2H)-yl)-2-methyl-1H-inden-1-yl)(4-phenyl-2-methyl-1H-inden-1-yl) zirconium dichloride After putting 1.4 g of (4-(3,4-dihydroquinolin-1(2H)-yl)-2-methyl-1H-inden-1-yl)(4-phenyl-2-methyl-1H-inden-1-yl) dimethyl silane (2.67 mmol, rac:meso=1:1) in a 100 mL Schlenk flask and dissolving the starting material by adding 30 mL of dry diethyl ether thereto, 2.4 mL of n-BuLi (2.5 M in n-Hx) was added thereto at −78° C. and the mixture was stirred at room temperature through the night. And then, the mixture was filtered by using a glass frit (G4). The remaining solid on the glass frit was vacuum dried and the lithiated product of white solid was obtained. After putting the lithiated product and ZrCl$_4$ (0.69 g, 2.94 mmol) in a 100 mL Schlenk flask in a glove box, 15 mL of dry hexane and 15 mL of diethyl ether were added thereto in order at −78° C. and the mixture was stirred at room temperature through the night. After the reaction was terminated, the product was filtered with a glass frit (G4) on which celite spread. The remaining solid on the glass frit was dissolved out by using dichloromethane (DCM). The red solid was obtained by vacuum drying the DCM filtrate. As the result of $^1$H-NMR analysis, the solid was Zr complex of rac:meso=1:1. The crude product was collected and recrystallized with dry toluene and hexane in a freezer of −30° C. for 3 days. The obtained red solid was filtered with a glass frit (G4) and washed twice with 10 mL of dry n-hexane, and then 0.2 g of the final product (11% yield) of racemic body was obtained by vacuum drying the solid.

$^1$H-NMR (CDCl$_3$): δ 7.61~7.30 (m, 8H), 7.14 (d, 1H), 7.07~6.99 (m, 3H), 6.88 (s, 1H), 6.80~6.75 (m, 1H), 6.63 (t, 1H), 6.57 (s, 1H), 6.29 (d, 1H), 3.79~3.75 (m, 2H), 2.83~2.78 (m, 2H), 2.23 (s, 3H), 2.18 (s, 3H), 2.05~1.94 (m, 2H), 1.29 (s, 6H).

Example 2

Synthesis of rac-dimethylsilylene-(4-(3,4-dihydroquinolin-1(2H)-yl)-2-methyl-1H-inden-1-yl)(4-phenyl-2-methyl-1H-inden-1-yl) hafnium dichloride After putting 1.6 g of (4-(3,4-dihydroquinolin-1(2H)-yl)-2-methyl-1H-inden-1-yl)(4-phenyl-2-methyl-1H-inden-1-yl) dimethyl silane of Example 1-3 (3.05 mmol, rac:meso=1:1) in a 100 mL Schlenk flask and dissolving the starting material by adding 40 mL of dry diethyl ether thereto, 2.7 mL of n-BuLi (2.5 M in n-Hx) was added thereto at −78° C. and the mixture was stirred at room temperature through the night. And then, the mixture was filtered by using a glass frit (G4). The remaining solid on the glass frit was vacuum dried and the lithiated product of white solid was obtained. After putting the lithiated product and HfCl$_4$ (1.1 g, 3.36 mmol) in a 100 mL Schlenk flask in a glove box, 20 mL of dry hexane and 20 mL of diethyl ether were added thereto in order at −78° C. and the mixture was stirred at room temperature through the night. After the reaction was terminated, the product was filtered with a glass frit (G4) on which celite spread. The remaining solid on the glass frit was dissolved out by using dichloromethane (DCM). The red solid was obtained by vacuum drying the DCM filtrate. As the result of $^1$H-NMR analysis, the solid was Hf complex of rac:meso=1:1. After collecting the crude product and storing the same in the oil bath of 45° C., 30 mL of dry toluene was added thereto with stirring for dissolving the same. The solution was stored in a freezer of −30° C. for 3 days for recrystallization. The obtained red solid was filtered with a glass frit (G4) and washed twice with 10 mL of dry n-hexane, and then 0.4 g of the final product (17% yield) of racemic body was obtained by vacuum drying the solid.

$^1$H-NMR (CDCl$_3$): δ 7.64 (td, 1H), 7.57~7.55 (m, 2H), 7.41~7.38 (m, 3H), 7.32~7.27 (m, 3H), 7.15~7.09 (m, 2H), 7.04~6.97 (m, 3H), 6.80 (t, 1H), 6.62 (td, 1H), 6.48 (s, 1H), 3.76~3.75 (m, 2H), 2.82~2.78 (m, 2H), 2.31 (s, 3H), 2.27 (s, 3H), 2.06~1.91 (m, 2H), 1.28 (s, 6H).

Example 3

Example 3-1: Synthesis of (4-(3,4-dihydroquinolin-1(2H)-yl)-2-methyl-1H-inden-1-yl)(4-naphthyl-2-methyl-1H-inden-1-yl) dimethyl silane After putting 1-(2-methyl-1H-inden-4-yl)-1,2,3,4-tetrahydroquinole of Example 1-1 (3.0 g, 11.5 mmol) in a 100 mL Schlenk flask and dissolving the starting material by adding 60 mL of dry diethyl ether thereto, n-BuLi (2.5 M in n-Hx) (5.1 mL) was added thereto at −78° C. and the mixture was stirred at room temperature through the night. And then, the mixture was filtered by using a glass frit (G4). The remaining solid on the glass frit was vacuum dried and the lithiated product (3.0 g, 98% yield) of white solid was obtained. After putting the lithiated product (3.0 g, 11.2 mmol), chloro(2-methyl-4-naphthyl-1H-inden-1-yl) dimethyl silane (3.9 g, 11.2 mmol), and copper cyanide (0.036 g, 0.40 mmol) in a 250 mL Schlenk flask in a glove box, 110 mL of dry diethyl ether was added thereto at −78° C. and the mixture was stirred at room temperature through the night. The reaction was terminated by adding 150 mL of aqueous NH$_4$Cl and 150 mL of deionized water after the reaction.

After separating the organic layer from water layer, the ligand compound of light yellowish solid (6.3 g, quantitative yield compared to the lithiated product, 98% yield compared to the starting material) was obtained by drying the organic layer with MgSO$_4$ and filtering and vacuum drying the same. As the result of $^1$H-NMR analysis, the ratio of rac:meso was about 1:1.

$^1$H-NMR (CDCl$_3$): δ 7.90~7.02 (m, 30H in rac- and meso-isomers), 6.86~6.83 (m, 2H in rac- and meso-isomers), 6.60 (t, 2H in rac- and meso-isomers), 6.50~6.48 (m, 2H in rac- and meso-isomers), 6.31~6.29 (s, 2H in rac- and meso-isomers), 3.88~3.80 (m, 4H in rac- and meso-isomers), 3.67~3.58 (m, 4H in rac- and meso-isomers), 2.92~2.89 (m, 4H in rac- and meso-isomers), 2.25~2.06 (m, 16H in rac- and meso-isomers), −0.18~−0.23 (m, 12H in rac- and meso-isomers).

Example 3-2: Synthesis of rac-dimethylsilylene-(4-(3,4-dihydroquinolin-1(2H)-yl)-2-methyl-1H-inden-1-yl)(4-naphthyl-2-methyl-1H-inden-1-yl) zirconium dichloride After putting 2.9 g of (4-(3,4-dihydroquinolin-1(2H)-yl)-2-methyl-1H-inden-1-yl)(4-naphthyl-2-methyl-1H-inden-1-yl) dimethyl silane (5.05 mmol, rac:meso=1:1) in a 100 mL Schlenk flask and dissolving the starting material by adding 50 mL of dry diethyl ether thereto, 4.5 mL of n-BuLi (2.5 M in n-Hx) was added thereto at −78° C. and the mixture was stirred at room temperature through the night. And then, the mixture was filtered by using a glass frit (G4). The remaining solid on the glass frit was vacuum dried and the lithiated product of white solid was obtained. After putting the lithiated product and ZrCl$_4$ (1.3 g, 5.56 mmol) in a 100 mL Schlenk flask in a glove box, 20 mL of dry hexane and 20 mL of diethyl ether were added thereto in order at −78° C. and the mixture was stirred at room temperature through the night. After the reaction was terminated, the product was filtered with a glass frit (G4) on which celite spread. The remaining solid on the glass frit was dissolved out by using dichloromethane (DCM). The red solid was obtained by vacuum drying the DCM filtrate. As the result of $^1$H-NMR analysis, the solid was Zr complex of rac:meso=3:1. The crude product was collected and recrystallized with dry toluene and pentane in a freezer of −30° C. for 3 days. The obtained red solid was filtered with a glass frit (G4) and washed twice with 10 mL of dry n-pentane, and then 1.07 g of the final product (29% yield) of racemic body was obtained by vacuum drying the solid.

$^1$H-NMR (CDCl$_3$): δ 7.86~6.77 (m, 17H), 6.59 (s, 1H), 6.40 (s, 1H), 3.81~3.72 (m, 2H), 2.85~2.82 (m, 2H), 2.23 (s, 3H), 2.15 (s, 3H), 2.10~1.95 (m, 2H), 1.32 (s, 3H), 1.29 (s, 3H).

Example 4

Synthesis of rac-dimethylsilylene-(4-(3,4-dihydroquinolin-1(2H)-yl)-2-methyl-1H-inden-1-yl)(4-naphthyl-2-methyl-1H-inden-1-yl)hafnium dichloride After putting 2.7 g of (4-(3,4-dihydroquinolin-1(2H)-yl)-2-methyl-1H-inden-1-yl)(4-naphthyl-2-methyl-1H-inden-1-yl) dimethyl silane of Example 3-1 (4.70 mmol, rac:meso=1:1) in a 100 mL Schlenk flask and dissolving the starting material by adding 25 mL of dry diethyl ether thereto, 4.14 mL of n-BuLi (2.5 M in n-Hx) was added thereto at −78° C. and the mixture was stirred at room temperature through the night. And then, the mixture was filtered by using a glass frit (G4). The remaining solid on the glass frit was vacuum dried and the lithiated product of white solid was obtained. After putting the lithiated product and HfCl$_4$ (1.66 g, 5.18 mmol) in a 100 mL Schlenk flask in a glove box, 20 mL of dry hexane and 350 mL of diethyl ether were added thereto in order at −78° C. and the mixture was stirred at room temperature through the night. After the reaction was terminated, the product was filtered with a glass frit (G4) on which celite spread. The remaining solid on the glass frit was dissolved out by using dichloromethane (DCM). The orange solid was obtained by vacuum drying the DCM filtrate. As the result of $^1$H-NMR analysis, the solid was Hf complex of rac:meso=4:1. The crude product was collected and recrystallized with dry toluene and pentane in a freezer of −30° C. for 3 days. The obtained yellow solid was filtered with a glass frit (G4) and washed twice with 10 mL of dry n-pentane, and then 1.00 g of the final product (26% yield) of racemic body was obtained by vacuum drying the solid.

$^1$H-NMR (CDCl$_3$): δ 7.85~6.62 (m, 17H), 6.50 (s, 1H), 6.31 (s, 1H), 3.75~3.74 (m, 2H), 2.84~2.82 (m, 2H), 2.32 (s, 3H), 2.23 (s, 3H), 2.07~1.92 (m, 2H), 1.31 (s, 3H), 1.28 (s, 3H).

Example 5

Example 5-1: Synthesis of (4-(indoline-1(2H)-yl)-2-methyl-1H-inden-1-yl)(4-naphthyl-2-methyl-1H-inden-1-yl) dimethyl silane After putting 1-(2-methyl-1H-inden-4-yl)-indoline (0.43 g, 1.73 mmol) in a 100 mL Schlenk flask and dissolving the starting material by adding 8.7 mL of dry diethyl ether thereto, n-BuLi (2.5 M in n-Hx) (0.76 mL) was added thereto at −78° C. and the mixture was stirred at room temperature through the night. And then, the mixture was filtered by using a glass frit (G4). The remaining solid on the glass frit was vacuum dried and the lithiated product (0.42 g, 96% yield) of white solid was obtained. After putting the lithiated product (0.42 g, 1.66 mmol), chloro(2-methyl-4-naphthyl-1H-inden-1-yl) dimethyl silane (0.58 g, 1.66 mmol), and copper cyanide (6.0 mg, 0.067 mmol) in a 1000 mL Schlenk flask in a glove box, 16 mL of dry diethyl ether was added thereto at −78° C. and the mixture was stirred at room temperature through the night. The reaction was terminated by adding 20 mL of deionized water after the reaction.

After separating the organic layer from water layer, the ligand compound of light yellowish solid (0.79 g, quantitative yield compared to the lithiated product, 85% yield compared to the starting material) was obtained by drying the organic layer with MgSO$_4$ and filtering and vacuum drying the same. As the result of $^1$H-NMR analysis, the ratio of rac:meso was about 1:1.

$^1$H-NMR (CDCl$_3$): δ 7.93~6.21 (m, 19H in rac- and meso-isomers), 3.75~3.54 (m, 4H in rac- and meso-isomers), 2.90~2.76 (m, 2H in rac- and meso-isomers), 2.01~1.75 (m, 6H in rac- and meso-isomers), −0.17~−0.26 (m, 6H in rac- and meso-isomers).

Example 5-2: Synthesis of rac-dimethylsilylene-(4-(indoline-1(2H)-yl)-2-methyl-1H-inden-1-yl)(4-naphthyl-2-methyl-1H-inden-1-yl) zirconium dichloride After putting 1.6 g of (4-(3,4-dihydroquinolin-1(2H)-yl)-2-methyl-1H-inden-1-yl)(4-phenyl-2-methyl-1H-inden-1-yl) dimethyl silane of Example 1-3 (3.05 mmol, rac:meso=1:1) in a 100 mL Schlenk flask and dissolving the starting material by adding 40 mL of dry diethyl ether thereto, 2.7 mL of n-BuLi (2.5 M in n-Hx) was added thereto at −78° C. and the mixture was stirred at room temperature through the night. And then, the mixture was filtered by using a glass frit (G4). The remaining solid on the glass frit was vacuum dried and the lithiated product of white solid was obtained. After putting the lithiated product and HfCl$_4$ (1.1 g, 3.36 mmol) in a 100 mL Schlenk flask in a glove box, 20 mL of dry hexane and 20 mL of diethyl ether were added thereto in order at −78° C. and the mixture was stirred at room temperature through the night. After the reaction was terminated, the product was filtered with a glass frit (G4) on which celite spread. The remaining solid on the glass frit was dissolved out by using dichloromethane (DCM). The red solid was obtained by vacuum drying the DCM filtrate. As the result of 1H-NMR analysis, both of two solids were the solid was Hf complex of rac:meso=1:1. After collecting the crude product and storing the same in the oil bath of 45° C., 30 mL of dry toluene was added thereto with stirring for dissolving the same. The solution was stored in a freezer of −30° C. for 3 days for recrystallization. The obtained red solid was filtered with a glass frit (G4) and washed twice with 10 mL of dry n-hexane, and then 0.4 g of the final product (17% yield) of racemic body was obtained by vacuum drying the solid.

$^1$H-NMR (toluene-d$_6$): δ 8.20~8.18 (dd, 1H), 7.75 (d, 1H), 7.58 (d, 1H), 7.49 (d, 1H), 7.30~6.87 (m, 1H), 6.75~6.70 (m, 2H), 6.53 (s, 1H), 4.14~4.03 (m, 2H), 2.73~2.71 (m, 2H), 2.12 (s, 3H), 1.88 (s, 3H), 0.91 (s, 3H), 0.86 (s, 3H).

Example 6

Synthesis of rac-dimethylsilylene-(4-(indoline-1(2H)-yl)-2-methyl-1H-inden-1-yl)(4-naphthyl-2-methyl-1H-inden-1-yl) hafnium dichloride After putting 2.0 g of (4-(indoline-1(2H)-yl)-2-methyl-1H-inden-1-yl)(4-naphthyl-2-methyl-1H-inden-1-yl) dimethyl silane of Example 5-1 (3.57 mmol, rac:meso=1:1) in a 100 mL Schlenk flask and dissolving the starting material by adding 18 mL of dry diethyl ether thereto, 3.14 mL of n-BuLi (2.5 M in n-Hx) was added thereto at −78° C. and the mixture was stirred at room temperature through the night. And then, the mixture was filtered by using a glass frit (G4). The remaining solid on the glass frit was vacuum dried and the lithiated product of white solid was obtained. After putting the lithiated product and HfCl$_4$ (1.26 g, 3.93 mmol) in a 100 mL Schlenk flask in a glove box, 18 mL of dry toluene was added thereto at −78° C. and the mixture was stirred at room temperature through the night. After the reaction was terminated, the product was filtered with a glass frit (G4) on which celite spread. The remaining solid on the glass frit was dissolved out by using dichloromethane (DCM). The orange solid was obtained by vacuum drying the DCM filtrate. As the result of $^1$H-NMR analysis, the solid was Hf complex of rac:meso=3:1. The crude product was collected and recrystallized with dry toluene in a freezer of −30° C. for 3 days. The obtained yellow solid was filtered with a glass frit (G4) and washed twice with 10 mL of dry toluene, and then 0.3 g of the final product (10% yield) of racemic body was obtained by vacuum drying the solid.

$^1$H-NMR (toluene-d$_6$): δ 8.12 (d, 1H), 7.76 (d, 1H), 7.62 (d, 1H), 7.55 (d, 1H), 7.51 (d, 1H), 7.27~6.85 (m, 10H), 6.70~6.67 (m, 2H), 6.42 (s, 1H), 4.07~3.98 (m, 2H), 2.70~2.67 (m, 2H), 2.19 (s, 3H), 1.95 (s, 3H), 0.88 (s, 3H), 0.84 (s, 3H), Comparative Example 1 rac-1,1'-dimethtylsilylene-bis(indenyl) hafnium dichloride rac-1,1'-dimethtylsilylene-bis(indenyl) hafnium dichloride compound was synthesized according to Example 1 disclosed in U.S. Pat. No. 5,905,162.

Preparation of Propylene Homopolymer

Example 7

After putting toluene solvent (0.2 L) in a 250 mL miniclave reactor, the temperature of the reactor was preheated to 70° C. After putting 0.2 mL of 5×10$^{-6}$ M dimethylanilinium tetrakis(pentafluorophenyl) borate co-catalyst in the reactor with a syringe, the transition metal compound of Example 1 ($1\times10^{-6}$M, 0.1 mL) treated with triisobutylaluminum compound was put in the reactor. The reaction was carried out for 10 mins while injecting 5 bar propylene therein. After carrying out the reaction for 10 mins, the remaining gas was removed therefrom and the precipitation was induced by adding the polymer solution to an excess of ethanol and cooling the same. The obtained polymer was washed with ethanol and acetone respectively twice or thrice and dried for 12 hrs or more in a vacuum oven of 80° C. And then, the properties of the polymer were measured.

Example 8

The olefin polymer was prepared according to the same method as in Example 7, except that the transition metal compound of Example 2 was used.

Example 9

The olefin polymer was prepared according to the same method as in Example 7, except that the transition metal compound of Example 3 was used.

Example 10

The olefin polymer was prepared according to the same method as in Example 7, except that the transition metal compound of Example 4 was used.

Comparative Example 2

The olefin polymer was prepared according to the same method as in Example 7, except that the amount of $5\times10^{-6}$ M dimethylanilinium tetrakis(pentafluorophenyl) borate co-catalyst was 1.0 mL and the transition metal compound of Comparative Example 1 ($1\times10^{-6}$M, 0.5 mL) treated with triisobutylaluminum compound was used.

The melting points (Tm) of the polymers were measured by using Q100 of TA Co., Ltd. The values were obtained during the second heating scan of 10° C./min, for eliminating the thermal history of the polymers.

The properties of the polymers of Examples 7 to 10 and Comparative Example 2 were measured by the method, and the results are listed in the following Table 1.

TABLE 1

|  | Catalytic activity (unit: kg/mmol hr) | Weight of polymer (unit: g) | Tm (unit: ° C.) |
| --- | --- | --- | --- |
| Example 7 | 474 | 7.9 | 147.8 |
| Example 8 | 432 | 7.2 | 148.4 |
| Example 9 | 156 | 7.8 | 149.5 |
| Example 10 | 134 | 6.7 | 155 |
| Comparative Example 2 | 151 | 12.6 | 122.5 |

Referring to Table 1, the propylene polymers prepared in Examples 7 to 10 show higher melting point (Tm) in comparison to the polymer of Comparative Example 2. Namely, it is recognized that the catalyst shows high catalytic activity and the olefin polymer having high isotacticity is obtained when the transition metal composition of the present invention is used as the catalyst.

Preparation of Propylene-Ethylene Copolymer

Example 11

After putting toluene solvent (0.8 L), propylene (250 g), and ethylene (70 psi) in a 2 L autoclave reactor, the pressure was adjusted to 500 psi with high pressure argon and the temperature of the reactor was preheated to 70° C. After putting 0.2 mL of $5\times10^{-6}$ M dimethylanilinium tetrakis (pentafluorophenyl) borate co-catalyst in the reactor with high pressure argon, the transition metal compound of Example 1 ($1\times10^{-6}$M, 0.1 mL) treated with triisobutylaluminum compound was put in a catalyst storage tank and subsequently put in the reactor by providing high pressure argon. The reaction was carried out for 10 mins. The heat of reaction was eliminated through a cooling coil inside the reactor and the polymerization temperature was maintained as uniform as possible. After carrying out the reaction for 10 mins, the remaining gas was removed therefrom, the polymer solution was drained through the bottom of the reactor, and the precipitation was induced by adding an excess of ethanol to the polymer solution and cooling the same. The obtained polymer was washed with ethanol and acetone respectively twice or thrice and dried for 12 hrs or more in a vacuum oven of 80° C. And then, the properties of the polymer were measured.

Example 12

The olefin polymer was prepared according to the same method as in Example 11, except that the transition metal compound of Example 3 was used.

Example 13

The olefin polymer was prepared according to the same method as in Example 11, except that the transition metal compound of Example 5 was used.

Comparative Example 3

The olefin polymer was prepared according to the same method as in Example 11, except that the amount of $5\times10^{-6}$ M dimethylanilinium tetrakis(pentafluorophenyl) borate co-catalyst was 1.0 mL and the transition metal compound of Comparative Example 1 ($1\times10^{-6}$M, 0.5 mL) treated with triisobutylaluminum compound was used.

The melt flow rates (MFR) of the polymers were measured by ASTM D-1238 (condition E, 230° C., 2.16 kg load). The melting points (Tm) were measured by using Q100 of TA Co., Ltd. The values were obtained during the second heating scan of 10° C./min, for eliminating the thermal history of the polymers.

The properties of the polymers of Examples 11 to 13 and Comparative Example 3 were measured by the method, and the results are listed in the following Table 2.

TABLE 2

|  | Catalytic activity (unit: kg/mmol hr) | Weight of polymer (unit: g) | Density (unit: g/cc) | Tm (unit: ° C.) | MFR (unit: g/10 min) |
| --- | --- | --- | --- | --- | --- |
| Example 11 | 5640 | 56.4 | 0.861 | 53.8 | 15.2 |
| Example 12 | 4860 | 81.0 | 0.865 | 53.1 | 10.2 |
| Example 13 | 8268 | 82.7 | 0.860 | 53.3 | 30.0 |
| Comparative Example 3 | 1040 | 86.6 | 0.856 | — | 13 |

Referring to Table 2, the propylene-ethylene polymers prepared in Examples 11 to 13 showed excellent properties such as higher catalytic activity and MFR in comparison to Comparative Example 3.

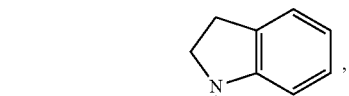
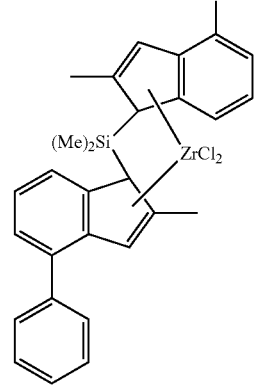
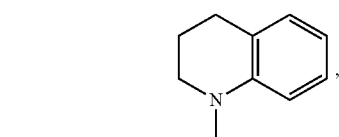
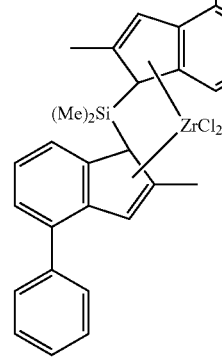
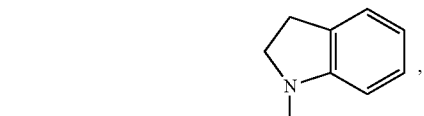
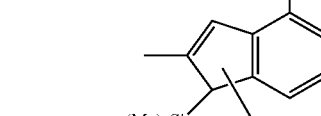
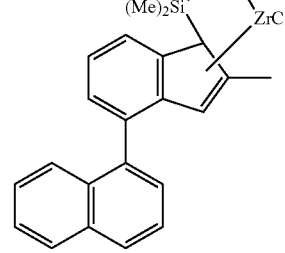

51
-continued
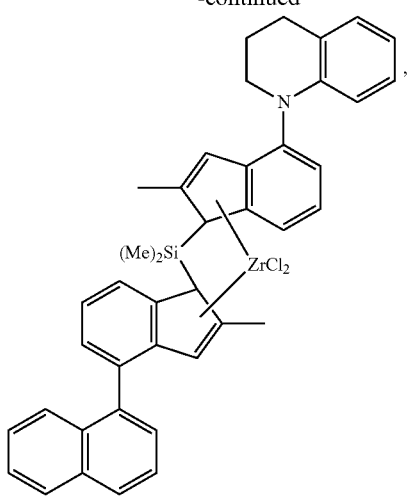
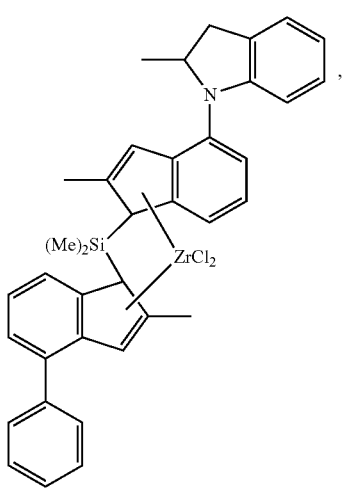
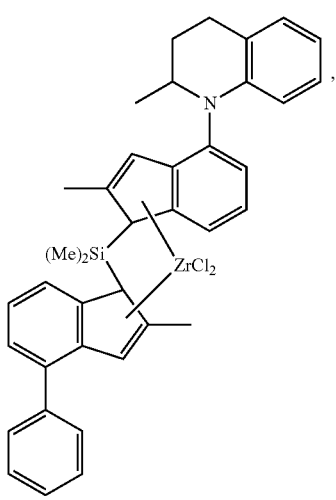
52
-continued
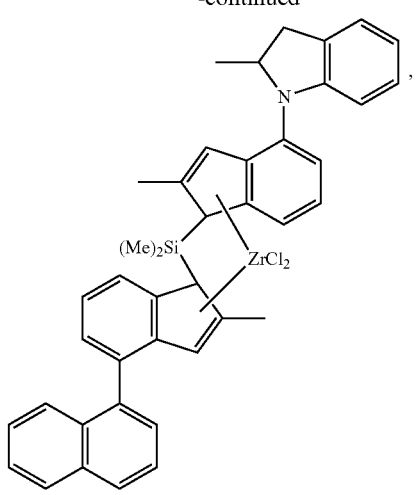
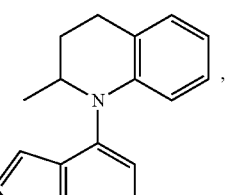
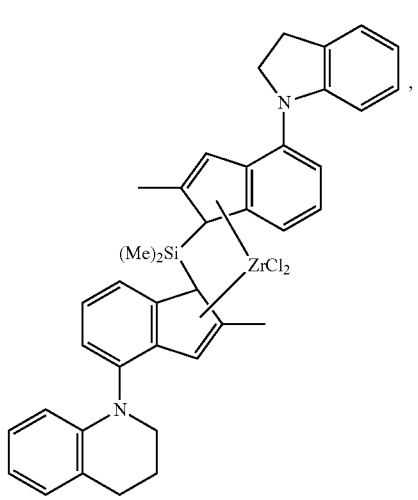

53
-continued
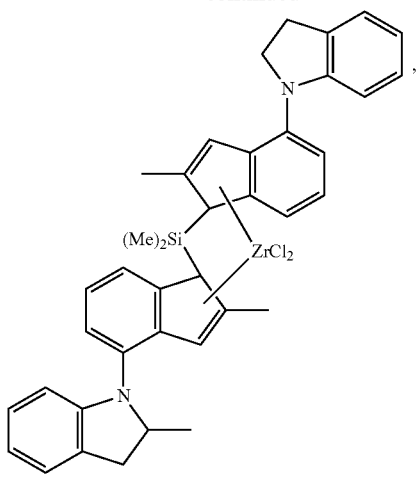
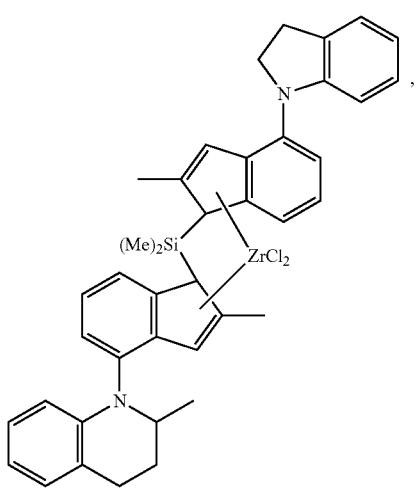
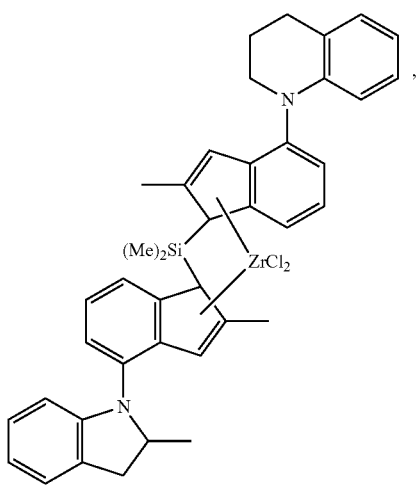
54
-continued
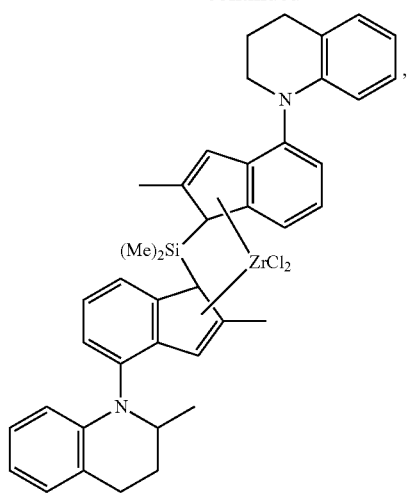
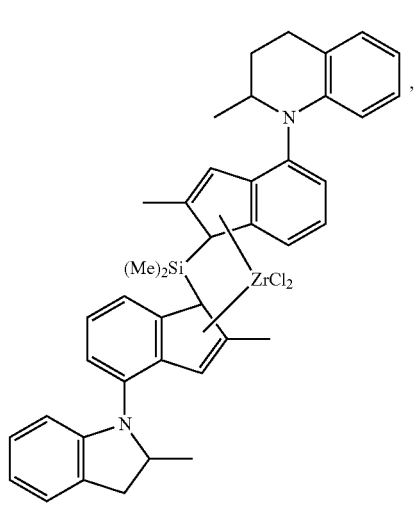
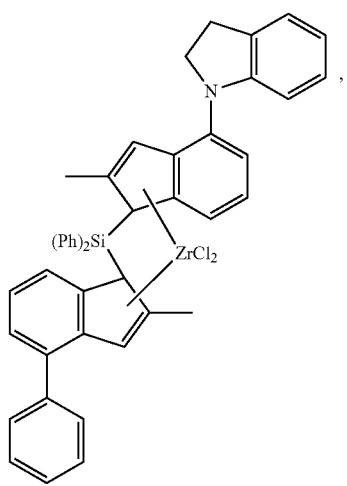

-continued
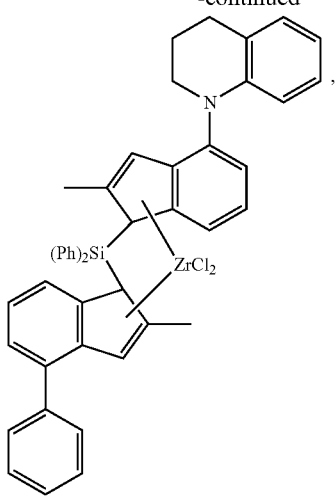
-continued
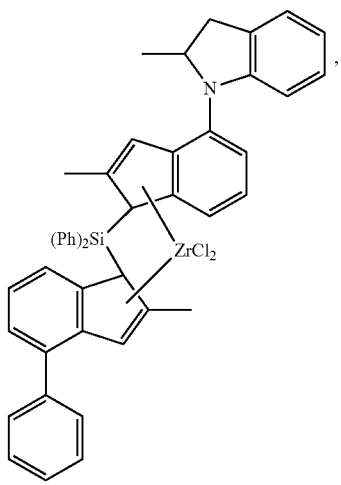
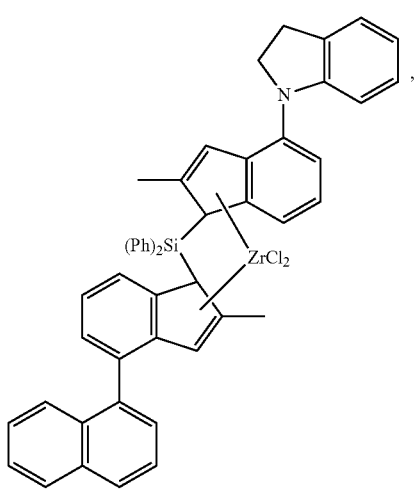
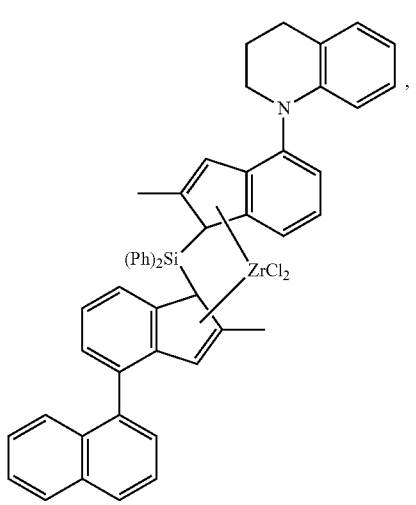

57
-continued
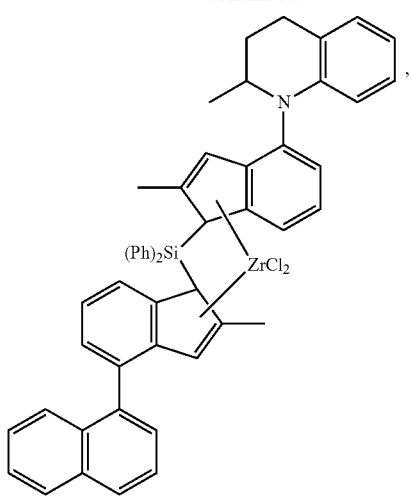
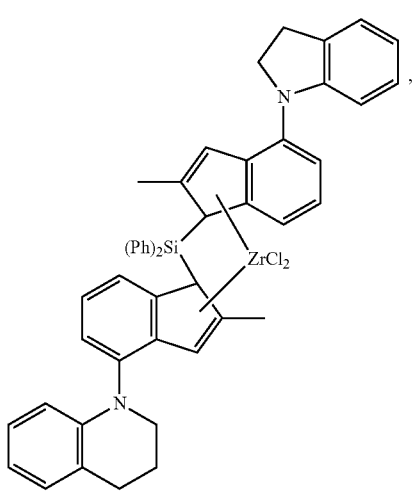
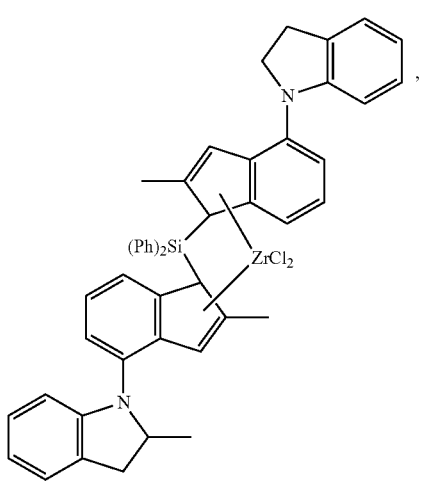
58
-continued
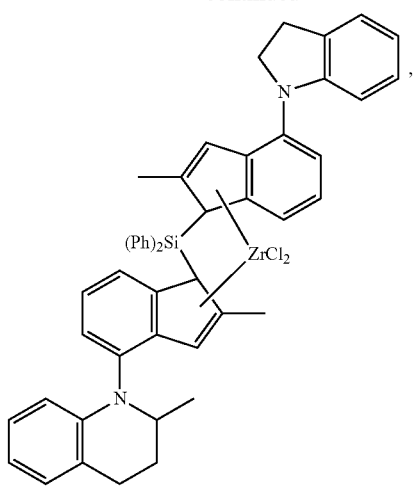
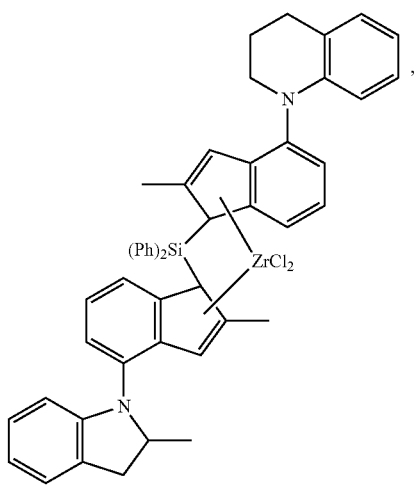
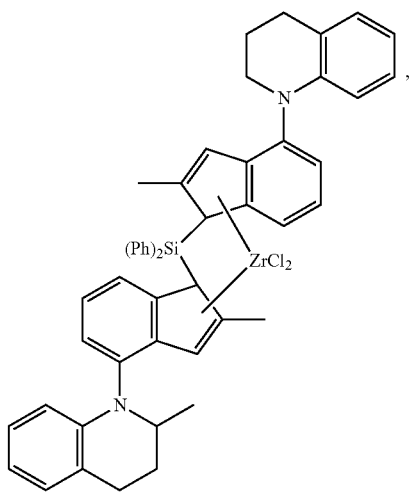

59
-continued
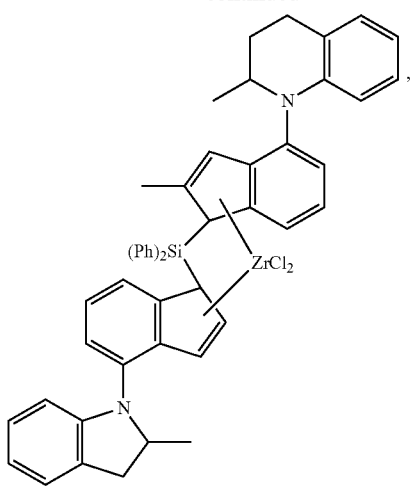
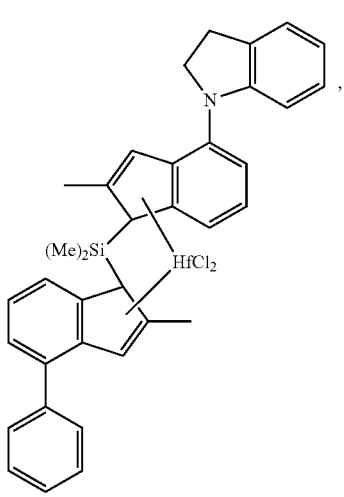
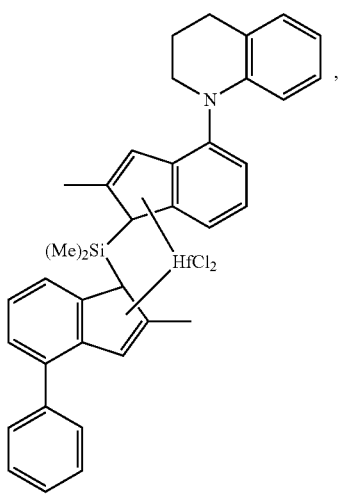
60
-continued
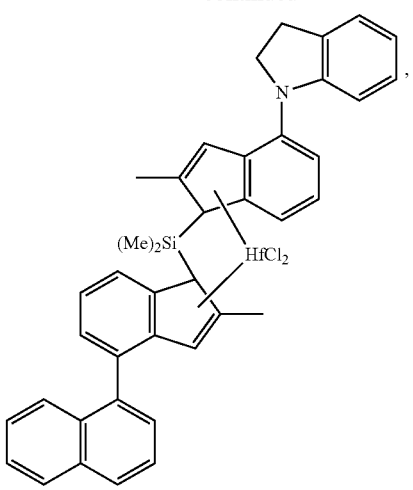
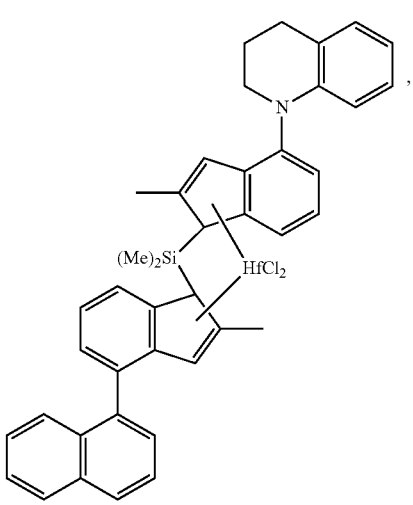
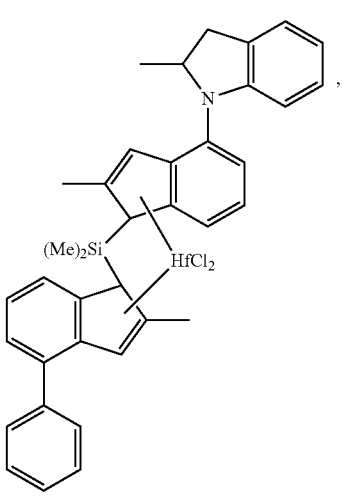

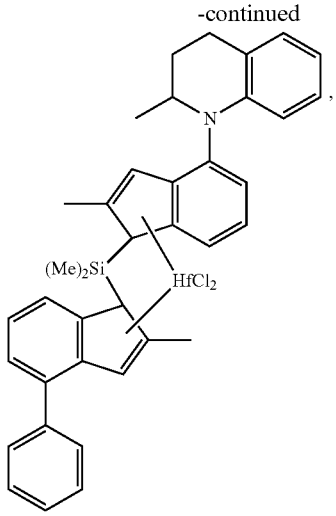
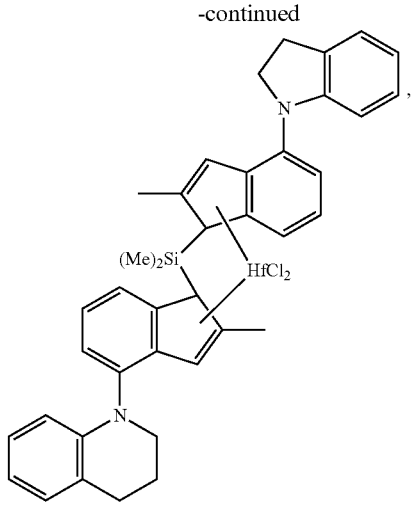
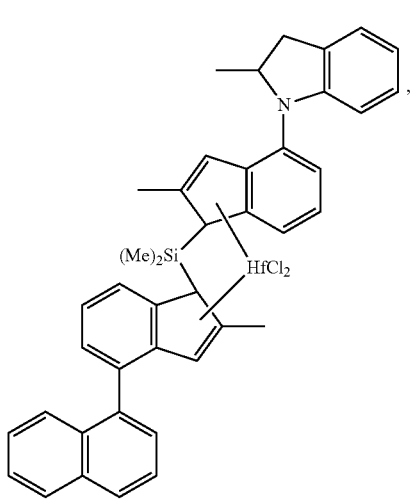
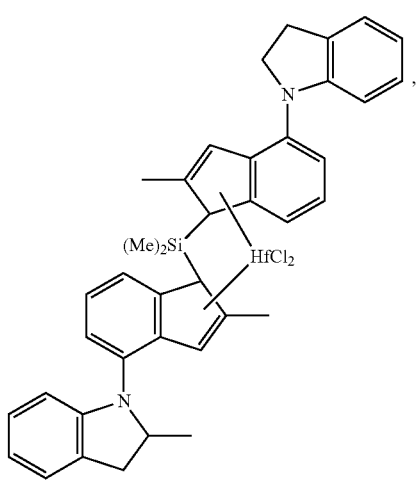
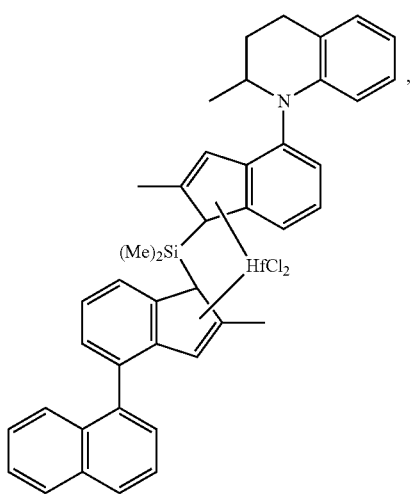
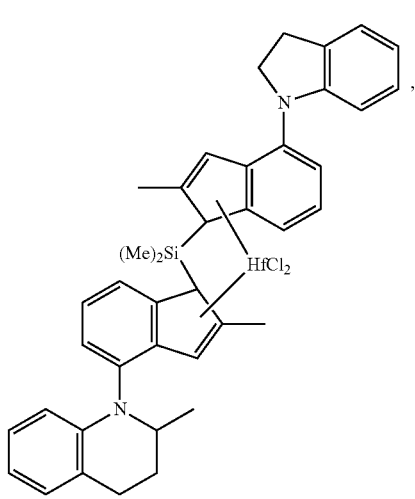

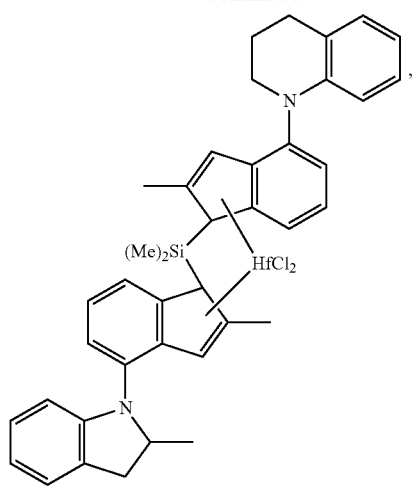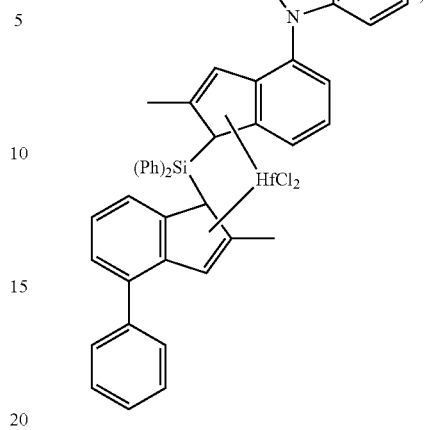

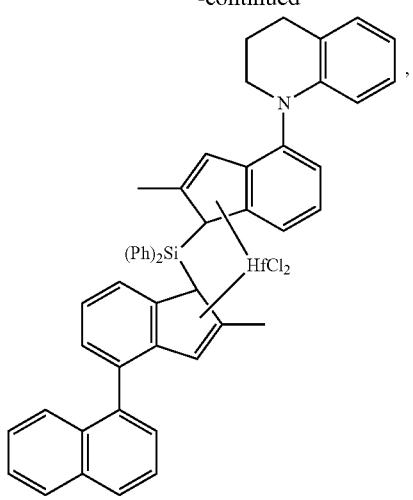
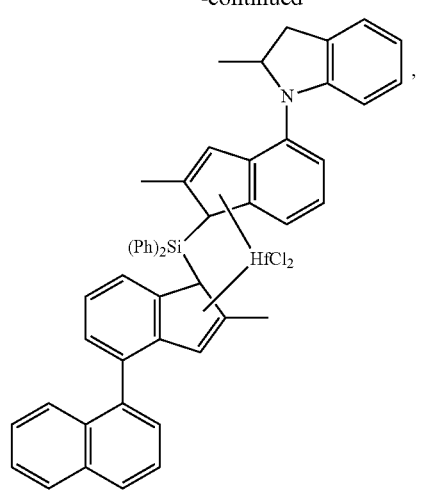
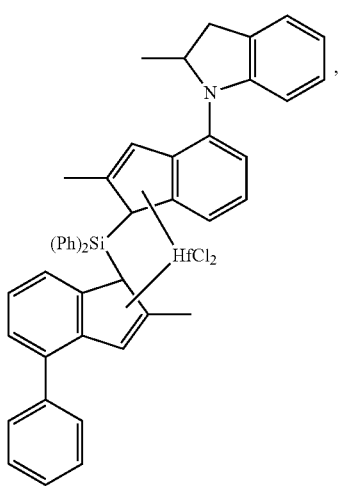
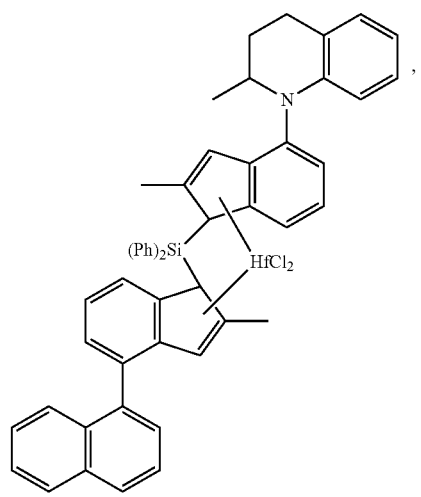
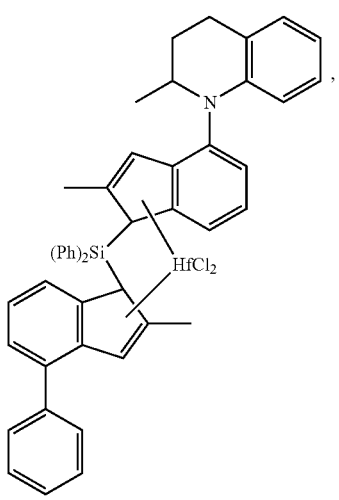
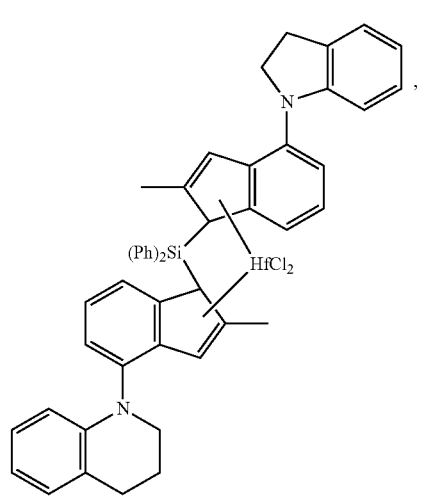

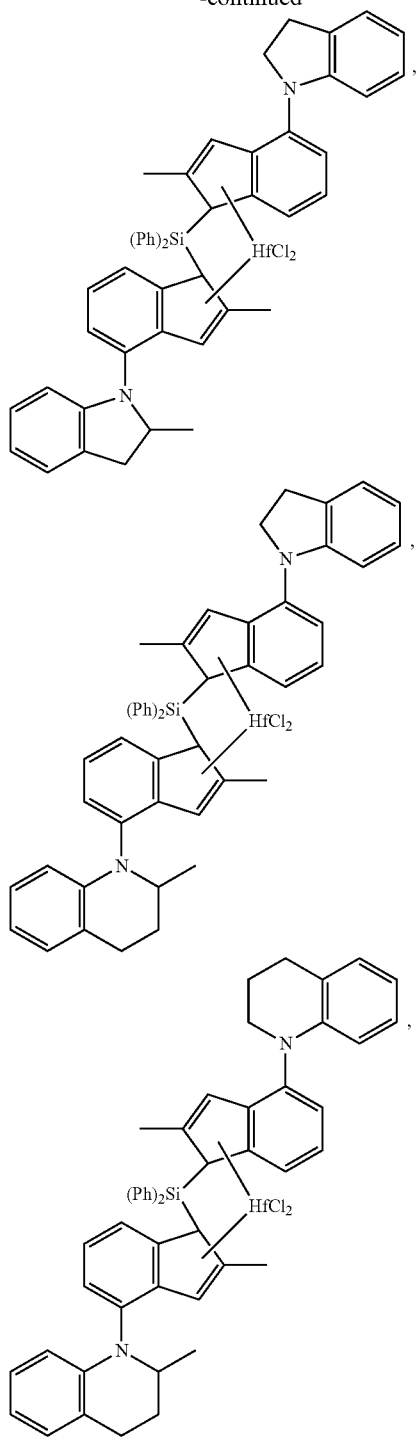
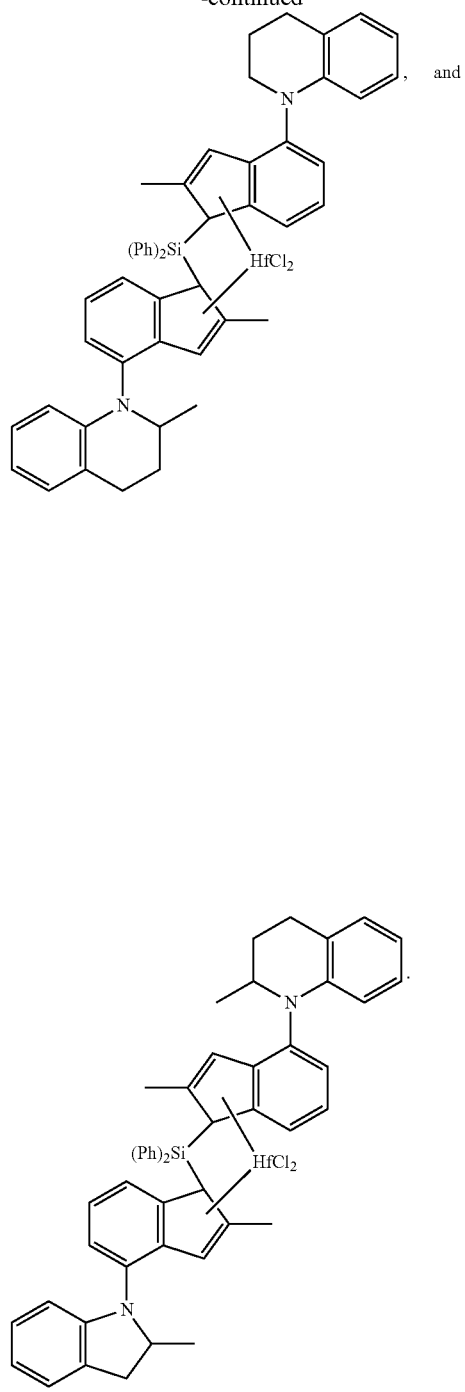

What is claimed is:

1. A transition metal compound, represented by the following Chemical Formula 2:

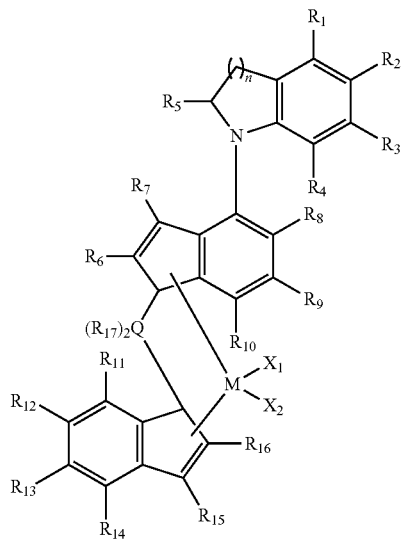

in Chemical Formula 2, n is an integer of 1 to 2;

$R_1$ to $R_{16}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, a $C_3$-$C_{20}$ cycloalkyl, a $C_5$-$C_{20}$ heteroring, or silyl, and 2 or more adjacent groups among $R_1$ to $R_{16}$ can be connected together via a $C_1$-$C_{20}$ alkyl group or a $C_6$-$C_{20}$ aryl group to form a ring;

$R_{17}$ is hydrogen, a halogen, a $C_1$-$C_{20}$ alkyl, a $C_6$-$C_{20}$ aryl, or a $C_1$-$C_{20}$ alkoxy;

Q is carbon or silicon;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

2. The transition metal compound according to claim 1, wherein $R_1$ to $R_{16}$ are independently hydrogen, a $C_1$-$C_{20}$ alkyl, a $C_6$-$C_{20}$ aryl, a $C_7$-$C_{20}$ alkylaryl, a $C_7$-$C_{20}$ arylalkyl, or a $C_5$-$C_{20}$ heteroring, and $R_{17}$ is a $C_1$-$C_{20}$ alkyl or a $C_6$-$C_{20}$ aryl.

3. The transition metal compound according to claim 1, wherein the M is a metal selected from the group consisting of Ti, Zr, and Hf.

4. The transition metal compound according to claim 1, wherein the transition metal compound represented by Chemical Formula 2 is represented by any one of the following structural formulae: